United States Patent
Tang et al.

(10) Patent No.: US 11,639,521 B2
(45) Date of Patent: May 2, 2023

(54) METHOD FOR DETERMINING THE COPY NUMBER OF A TANDEM REPEAT SEQUENCE

(71) Applicant: The Chinese University of Hong Kong, Hong Kong (CN)

(72) Inventors: Leung Sang Nelson Tang, Hong Kong (CN); Suk Ling Ma, Hong Kong (CN); Jean Woo, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 16/891,452

(22) Filed: Jun. 3, 2020

(65) Prior Publication Data

US 2021/0010069 A1    Jan. 14, 2021

Related U.S. Application Data

(60) Provisional application No. 62/856,449, filed on Jun. 3, 2019.

(51) Int. Cl.
*C12Q 1/6827* (2018.01)
*C12Q 1/6883* (2018.01)

(52) U.S. Cl.
CPC ......... *C12Q 1/6827* (2013.01); *C12Q 1/6883* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 7,695,904 B2 | 4/2010 | Cawthon |
| 9,347,094 B2 | 5/2016 | Litterst et al. |
| 9,944,978 B2 | 4/2018 | Harley et al. |
| 2011/0207128 A1 | 8/2011 | Cawthon et al. |
| 2013/0337447 A1* | 12/2013 | Porreca ............... C12Q 1/6886 435/6.11 |
| 2014/0370505 A1 | 12/2014 | Harley |
| 2016/0032360 A1 | 2/2016 | Keefe et al. |
| 2016/0194705 A1 | 7/2016 | Cawthon |

FOREIGN PATENT DOCUMENTS

| | | |
|---|---|---|
| EP | 2474822 A1 | 7/2012 |
| WO | 2010/075413 A1 | 7/2010 |
| WO | 2014/031908 A1 | 2/2014 |

OTHER PUBLICATIONS

Carlson et al Genome Research. 2015. 25: 750-761 (Year: 2015).*
Beh et al Nucleic Acids Research. 2018. 46(19): e117 and Supplementary Information, 31 pages (Year: 2018).*
Bergman, "Comparative Genomics," vol. 2, Methods in Molecular Biology (2007).
Cawthon, "Telomere measurement by quantitative PCR," Nucleic Acids Res., vol. 30(10), 6 pages (2002).
Cawthon, "Telomere length measurement by a novel monochrome multiplex quantitative PCR method," Nucleic Acids Research, vol. 37, No. 3, 7 pages (2009).
Hardenbol, et al., "Multiplexed genotyping with sequence-tagged molecular inversion probes," Nature Biotechnology, vol. 21, No. 6, pp. 673-678 (2003).
Martin-Ruiz, "Reproducibility of telomere length assessment: an international collaborative study," International Journal of Epidemiology, vol. 44, No. 5, pp. 1673-1683 (2015).
Nilsson, et al., "Padlock Probes: Circularizing Oligonucleotides for Localized DNA Detection," Science, vol. 265(5181), pp. 2085-2088 (Sep. 30, 1994).
Syvänen, "Toward genome-wide SNP genotyping," Nature Genetics Supplement, vol. 37, pp. S5-S10 (Jun. 2005).
Dweck, et. al., "The advancement of telomere quantification methods.," Mol Biol Rep., vol. 48(7), pp. 5621-5627 (Jul. 2021).

* cited by examiner

*Primary Examiner* — Carla J Myers
(74) *Attorney, Agent, or Firm* — Kilpatrick Townsend & Stockton LLP

(57) ABSTRACT

The present invention provides novel compositions and methods for assessing the size of tandem repeat sequences, e.g., telomeres, within a genome, using specially designed Molecular Inversion Probes (MIPs) and reaction conditions.

17 Claims, 11 Drawing Sheets

Specification includes a Sequence Listing.

Comparison of conventional MIP protocol and this invention

1. Large excess of MIP probe to give saturated binding to target motifs.

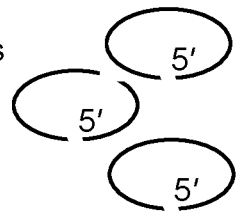

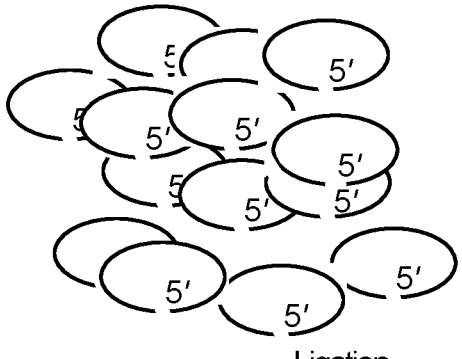

2. 2 type of ligation products and ligation points are counted.

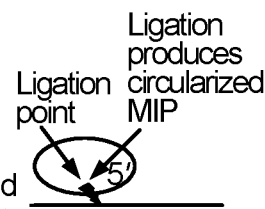

Ligation point / Ligation produces circularized MIP

Ligation point / Ligation produces circularized MIP

Another form of ligation product, ligated linear MIPs (LL-MIP)

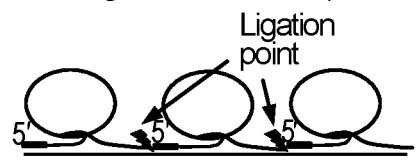

Ligation point

Therefore, avoidance of Exonuclease Or only exonuclease I to remove single strand probes.

Both types are used in assay

3. Target sequence for hybridization

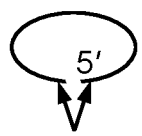

Different sequences at 5' and 3' of MIP probe

Conventional MIP protocol

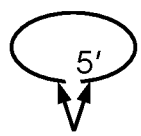

5' and 3' of MIP probe may bind to same sequence motif (e.g. 6 bp repeat motifs of telomere)

This invention

FIG. 4

SEQUENCE LISTING

```
<160> NUMBER OF SEQ ID NOS: 39

<210> SEQ ID NO 1
<211> LENGTH: 91
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
gttagggtta gggttagggt tacttcagct tcccgatccg acggtagtgt tcacacagga      60
aacagctatg actagggtta gggttagggt t                                    91

<210> SEQ ID NO 2
<211> LENGTH: 92
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 2
gttagggtta gggttagggt tacttcagct tcccgatccg acggtagtgt tcacacagga      60
aacagctatg actagggtta gggttagggt ta                                    92

<210> SEQ ID NO 3
<211> LENGTH: 84
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
ggttagggtt agggttactt cagcttcccg atccgacggt agtgttcaca caggaaacag      60
ctatgacggt tagggttagg gtta                                             84

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
gttagggtta gggttagggt ta                                               22

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
ggttagggtt agggtta                                                     17

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6 tagggtagg gttagggtt                                                    19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
tagggttagg gttagggtta                                                  20

<210> SEQ ID NO 8
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
ggttagggtt agggtta                                                    17

<210> SEQ ID NO 9
<211> LENGTH: 99
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
ggaaggaagg aaggaaggaa ggtcgatccg acagcttccg tagcggtttc acacaggaaa     60
cagctatgac tcacagaagg aaggaaggaa ggaaggaag                            99

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggtccgagcc agctatgact agggttaggg                                      30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcgcatgtga atcgggaagc tgaagtaacc                                      30

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gctgcctcgc aggaaacagc tatgactcac ag                                   32

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggtgcgtcgc gctgtcggat cgaccttcct t                                    31

<210> SEQ ID NO 14
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
tagggttagg gttagggtta gggt                                              24

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
aaggaaggaa ggaaggaagg                                                   20

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggcgcatggc tcacacagga aacagctatg ac                                     32

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcatggcgac aatcgggaag ctgaagccat ccat                                   34

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
ggttagggtt                                                              10

<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
gatggatgga t                                                            11

<210> SEQ ID NO 20
<211> LENGTH: 94
```

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
atggatggat ggatggatgg atggcttcag cttcccgatc cgacggttag gttcacacag    60
gaaacagcta tgacggatgg atggatggat ggat                               94

<210> SEQ ID NO 21
<211> LENGTH: 84
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
gatggatgga tggatggctt cagcttcccg atccgacggt taggttcaca caggaaacag    60
ctatgactgg atgatggat ggat                                           84

<210> SEQ ID NO 22
<211> LENGTH: 95
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
gaaggaagga aggaaggaag gggcgcttca gcttcccgat ccgacggtag tgttcacaca    60
ggaaacagct atgacaagga aggaaggaag gaagg                              95

<210> SEQ ID NO 23
<211> LENGTH: 99
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
ggaaggaagg aaggaaggaa ggtcgatccg acagcttccg tagcggtttc acacaggaaa    60
cagctatgac tcacagaagg aaggaaggaa ggaaggaag                          99

<210> SEQ ID NO 24
<211> LENGTH: 102
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
gtctaggttt gatgtgaaga tatcccgct tcagcttccc gatccgacgg taggtttcac     60
acaggaaaca gctatgactc acagaaaacg ttctgagaat gc                      102

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
gcgggcaggg cggctctaga tcacacagga aacagctatg ac                42

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggccctaccg tcggatcggg aagc                                    24

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggcctatgac tcacagaaaa cgttctgag                               29

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctaccgtcgg atcgggaag                                          19

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
gtctaggttt gatgtgaaga tatacccgct t                            31

<210> SEQ ID NO 30
<211> LENGTH: 556
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gcgcatgtga atcgggaagc tgaagtaacc ctaaccctaa ccctaaccct aaccctaacc      60
ctaaccctag tcatagctgt ttcctgtgtg aacactaccg tcggatcggg aagctgaagt    120
aaccctaacc ctaaccctaa ccctaaccct aaccctagtc atagctgttt cctgtgtgaa    180
cactaccgtc ggatcgggaa gctgaagtaa ccctaaccct aaccctaacc ctaaccctaa    240
ccctaaccct agtcatagct gtttccgtgt gaacactac cgtcggatcg ggaagcgaag    300

```
taacccta ac cctaacccta accctaacccc taacccta gt catagctgtt tcctgtgtga    360
acactaccgt cggatcggaa gctgaataac cctaacccta accctaaccc taacccta ac      420 cctaacccta gtcatagctg tttcctgtgt gaacactacc gtcggatcgg aagctgaag        480 taacccta ac cctaacccta accctaacccc taacccta ac cctagtcata gctgtttcct    540
gtgtgagcca tgcgcc                                                      556
```

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cccaatccca atcccaat                                                    18

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
gttagggtta gggttagggt t                                                21

<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tacctaccta cc                                                          12

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
atggatggat ggatggatgg atgg                                             24

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
ggatggatgg atgatggat                                                   20

<210> SEQ ID NO 36
<211> LENGTH: 14
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 36
gggttagggt tagg                                                         14

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
ggatggatgg                                                              10

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gcatggcgca atcgggaagc tgaagccatc cat                                    33

<210> SEQ ID NO 39
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gggttagggt tagggttagg gttagggtta gggttagggt tagggttagg gttagggtta       60
gggttagggt tagggttagg gttagggtta gggttagggt tagggtta                   108
```

METHOD FOR DETERMINING THE COPY NUMBER OF A TANDEM REPEAT SEQUENCE

CROSS REFERENCE TO RELATED APPLICATIONS

The present application claims priority to U.S. Provisional Pat. Appl. No. 62/856,449, filed on Jun. 3, 2019, which application is incorporated herein by reference in its entirety.

REFERENCE TO SUBMISSION OF A SEQUENCE LISTING AS A TEXT FILE

The Sequence Listing written in file 080015-1194498-027810US_SL.txt created on Sep. 29, 2020, 10,609 bytes, machine format IBM-PC, MS-Windows operating system, is hereby incorporated by reference in its entirety for all purposes.

BACKGROUND OF THE INVENTION

Molecular Inversion Probes, or MIPs, are single stranded DNA probes with both 5' and 3' ends targeting (complementary to) the same strand of a target template. The principle of MW assays in all previous applications makes use of the formation of a circularized product by a template-dependent ligation event that is specific to the template sequence in the sample and that is used to interrogate the sequence content of the sample. In order to remove non-specific MIPs, all non-circular products are removed after the ligation step, e.g., by a combination of DNA digestion enzymes such as exonuclease I and exonuclease III.

Classical MIP probes, and methods of using them, e.g., for nucleic acid detection and quantification, are not suitable, however, for use on tandem repeat sequences such as telomeres. Assays designed for use with classical MIP probes are based on the hybridization of the 5' and 3' ends of the MIPs to specific, invariable sites on the template DNA, with the 5' and 3' sequences hybridizing to different target sequences on the template DNA. In classical MIP-based approaches, the 5' and 3' ends are either immediately adjacent to one another upon binding to the same template, allowing their direct ligation and circularization, or are separated by one or more nucleotides, allowing their circularization following 3' end extension (also known as "gap filling") and subsequent ligation. In all such cases, the circularized products of such reactions are subsequently isolated from linear, i.e., non-ligated MIPs and non-circularized ligated MIPs, prior to their detection and/or quantification.

Because the 5' and 3' ends of MIPs directed to tandem repeat sequences would necessarily target the same, repeated sequence, such probes are not suitable for traditional MIP-based methods because they would permit promiscuous binding of the MIP ends to any of the numerous repeats within a given repeat array, separating the 5' and 3' ends by a highly variable number of intervening nucleotides within the template DNA and giving rise to a diverse set of products. In view of this diversity of products, and the fact that classical MIP-based assays involve the removal of all linear products prior to detection or quantification, classical MIP-based approaches would lead to highly inaccurate and unreliable results when used with tandem repeat sequences. Thus, no prior success has been shown with MIP-based interrogation of telomere length or of the length of other tandem repeat sequences.

The ability to measure the length of telomeres or other tandem repeat sequences of variable length is useful for many purposes, including as a biomarker for biological aging. Human telomeres consist of a 6-base pair repeat motif located at the ends of each chromosome. Telomeres shorten upon cell division, and their rate of attrition may be affected by diseases and health conditions. For example, the rate of their shortening may be influenced by lifestyle factors like diet, smoking, physical activity, and alcohol intake, as well as stress and psychosocial factors (Epel et al 2004; Starkweather et al 2013). Measurements of telomere length may therefore be useful for indicating an individual's biological age and the type of lifestyle changes that the individual could make in order to enjoy better health.

Various methods have been developed to measure telomere length, but each brings its own set of limitations and constraints. For example, the classical method for measuring telomere length is the telomere restriction fragment assay (TRF; Kimura et al 2010), which involves restriction digestion of the telomere from peripheral blood leukocytes, followed by Southern blotting. However, TRF is not suitable for handling large DNA sample sizes (Samani et al 2001, Valdes et al 2005), and results can be easily affected by, e.g., the type of gel electrophoresis used, the amount of DNA available, the quality of the image capturing device, and the computer software used for the analysis (Kimura et al 2010).

Another method for measuring telomere length is the T/S assay, which is based on real-time quantitative PCR and comparison with a reference sample. However, studies have shown that the originally provided coefficient of variation is underestimated, and that the quality of DNA, the PCR machine used, and the analytical software can affect the results (Aubert et al., 2012, Cunningham et al., 2013, Nussey et al., 2014). Other assays that have been used include quantitative fluorescence in-situ hybridization (Q-FISH) and flow cytometry FISH (Flow-FISH); these methods can permit high levels of precision, but are limited in that the blood samples analyzed must be freshly drawn, which is impractical, e.g., in terms of epidemiology studies.

There is therefore a need for new, reliable methods for measuring the length of telomeres or other tandem repeat sequences that can be applied at a large scale such as in epidemiology studies or for everyday routine hospital laboratory practice. The present invention addresses these and other needs.

BRIEF SUMMARY OF THE INVENTION

In one aspect, the present invention provides a single-stranded DNA probe for determining telomere length and/or the copy number of a tandem repeat sequence, wherein the probe comprises: i) a 5' homology region that extends to the 5' end of the probe and that comprises a nucleotide sequence complementary to the tandem repeat sequence; ii) a linker region; and iii) a 3' homology region that extends to the 3' end of the probe and that comprises a nucleotide sequence complementary to the tandem repeat sequence, such that the 5' homology region and 3' homology region can bind to the same strand of a template DNA comprising the tandem repeat sequence; wherein upon binding of the 5' homology region and the 3' homology regions to the same strand of a template DNA such that the 3' homology region is immediately 3' of the 5' homology region within a single repeat unit on the template, and the 3' end of the 3' homology region and the 5' end of the 5' homology region are thus separated by a nucleotide gap of less than one complete repeat unit on the template DNA, the nucleotide gap of less than one complete repeat unit comprises at most 2 different bases.

In some embodiments of the present invention, the tandem repeat sequence is a telomere sequence. In some embodiments, the telomere is a human telomere. In some embodiments, the nucleotide sequences of the 5' and 3' homology regions are 100% complementary to the tandem repeat sequence. In some embodiments, the 5' and 3' homology regions are each 15-25 nucleotides long. In some embodiments, each repeating unit of the tandem repeat sequence is 2-10 nucleotides long. In some embodiments, the linker region comprises one or more sequence elements selected from the group consisting of a common primer sequence, a probe-specific primer sequence, a TaqMan probe sequence, and a tag sequence.

In some embodiments of the present invention, the 3' end of the 3' homology region and the 5' end of the 5 homology region are separated by 1 or 2 nucleotides when bound within a single repeat unit on the template DNA. In some embodiments, the 1 or 2 nucleotides comprise the base G. In some embodiments, the 3' end of the 3' homology region and the 5' end of the 5' homology region are separated by 3 nucleotides when bound within a single repeat unit on the template DNA. In some embodiments, the 3 nucleotides comprise 2 different bases, and wherein the 2 different bases are A and G. In some embodiments, the 5' homology region comprises the nucleotide sequence of SEQ ID NO: 4 or SEQ ID NO: 5. In some embodiments, the 3' homology region comprises the nucleotide sequence of any one of SEQ ID NOS: 6-8. In some embodiments, the probe comprises the nucleotide sequence of any one of SEQ ID NOS: 1-3.

In another aspect, the present invention provides a kit for determining the copy number of a variable tandem repeat sequence within a genome, where the kit comprises: a first single-stranded DNA probe as described herein, wherein the 5' and 3' homology regions of the first DNA probe are complementary to a tandem repeat sequence with a copy number in the genome that varies between individuals; and a second single-stranded DNA probe as described herein, wherein the 5' and 3' homology regions of the second DNA probe are complementary to a tandem repeat sequence with a copy number in the genome that is stable between individuals; wherein the at most two bases comprised by the nucleotide gap of the first probe are also comprised by the nucleotide gap of the second probe.

In some embodiments, the kit further comprises a reaction mixture comprising DNA polymerase, an enzyme comprising ligase activity, and deoxyribonucleoside triphosphates corresponding to the at most two bases comprised by the nucleotide gaps of the first and second probes. In some embodiments, the DNA polymerase is T4 DNA polymerase. In some embodiments, the ligase activity is provided by Amp ligase. In some embodiments, the reaction mixture does not comprise an exonuclease enzyme. In some embodiments, the kit further comprises test sample genomic DNA. In some embodiments, the kit further comprises a common primer, two or more probe-specific primers, and/or two or more TaqMan probes complementary to a sequence within the linker region of the first and/or second probe.

In some embodiments of the present kits, the tandem repeat sequence recognized by the 5' and 3' homology regions of the first probe is a telomere sequence. In some embodiments, the telomere is a human telomere. In some embodiments, the tandem repeat sequence recognized by the 5' and 3' homology regions of the second probe is a 4-bp short tandem repeat. In some embodiments, the nucleotide sequences of the 5' and 3' homology regions of the first probe are 100% complementary to the tandem repeat sequence with a copy number in the genome that varies between individuals. In some embodiments, the nucleotide sequences of the 5' and 3' homology regions of the second probe are 100% complementary to the tandem repeat sequence with a copy number in the genome that is stable between individuals. In some embodiments, the 5' and/or 3' homology regions of the first and/or second probes are from 15 to 25 nucleotides long. In some embodiments, the repeating units of the tandem repeat sequences recognized by the first and/or second probes are 3-6 nucleotides long.

In another aspect, the present invention provides a method of determining the length of a tandem repeat sequence region of variable length in the genome of an individual, wherein the method comprises: i) providing a first single-stranded DNA probe as described herein, wherein the 5' and 3' homology regions of the first DNA probe are complementary to a tandem repeat sequence with a copy number in the genome that varies among individuals; and ii) providing a second single-stranded DNA probe as described herein, wherein the 5' and 3' homology regions of the second DNA probe are complementary to a tandem repeat sequence with a copy number in the genome that is stable among individuals; wherein the at most two bases comprised by the nucleotide gap of the first probe are also comprised by the nucleotide gap of the second probe; iii) contacting a biological sample from the individual with the first and second probes in the presence of a DNA polymerase, ligase activity, and at most two deoxyribonucleoside triphosphates corresponding to the bases comprised by the nucleotide gaps of the first and second probes, under conditions conducive to extension of the 3' end of the probes and ligation to the 5' end of a probe bound to the same template; iv) quantifying the circularized and ligated linear probe products generated in step iii) for the first and/or second probes; and v) using the relative quantities of the circularized and ligated linear probe products for the first and/or second probes to determine the normalized abundance of ligation points for the first and/or second probes, which is an indicator of the length of the tandem repeat corresponding to the probe in the genome of the individual.

In some embodiments of the present methods, the nucleotide sequences of the 5' and 3' homology regions of the first and second probes are 100% complementary to the first and second tandem repeat sequences, respectively. In some embodiments, the 5' and 3' homology regions of the probes are 15-25 nucleotides long. In some embodiments, the variable tandem repeat sequence region is the telomere. In some embodiments, the telomere is a human telomere. In some embodiments, the linker region of each the probes comprises one or more sequence elements selected from the group consisting of a common primer sequence, a probe-specific primer sequence, a TaqMan probe sequence, and a tag sequence. In some embodiments, the 3' end of the 3' homology region and the 5' end of the 5' homology region of the probes are separated by a gap of 1 or 2 nucleotides when bound within a single repeat unit on the tandem repeat sequence, wherein the 1 or 2 nucleotides comprise a single base, and wherein only one deoxyribonucleoside triphosphate corresponding to the single base is provided in step iii). In some embodiments, the single base is G. In some embodiments, the 3' end of the 3' homology region and the 5' end of the 5' homology region of the probe of step i) or the probe of step ii) are separated by a gap of 3 nucleotides when bound within a single repeat unit on the tandem repeat sequence, wherein the 3 nucleotides comprise 2 bases, and wherein two deoxyribonucleoside triphosphates corresponding to the two bases are provided in step iii). In some embodiments, the 2 bases are A and G.

In some embodiments of the present methods, the 5' homology region of the probe of step i) comprises the nucleotide sequence of SEQ ID NO: 4 or SEQ ID NO: 5. In some embodiments, the 3' homology region of the probe of step i) comprises the nucleotide sequence of any one of SEQ ID NOS: 6-8. In some embodiments, the probe of step i) comprises the nucleotide sequence of any one of SEQ ID NOS: 1-3. In some embodiments, a large excess of the probes of steps i) and ii) are provided relative to the quantity of genomic DNA in the biological sample. In some embodiments, no exonuclease is added during steps i) to v). In some embodiments, the only exonuclease added during steps i) to v) is exonuclease I, and wherein the level of exonuclease I does not exceed 20 units per 50 ng of genomic DNA and is present for a maximum of one hour. In some embodiments, the quantities of the circularized and ligated linear probe products for the probes are determined using a method selected from the group consisting of quantitative PCR, digital PCR, and sequencing. In some embodiments, only the first single stranded probe is used, and another method is used to quantify the amount of input sample DNA.

BRIEF DESCRIPTION OF THE DRAWINGS

FIG. 1A shows simple circularized MIPs in conventional MIP assays. FIG. 1B shows the other type of ligation product, LL-MIP. FIG. 1C shows the sequence of an example LL-MIP product after cloning of a PCR product, which shows 6 MIP probes were ligated together in this LL-MIP (SEQ ID NO: 30).

FIG. 4. Comparison to existing MIP assays, and the method to determine telomere length in this invention.

DETAILED DESCRIPTION OF THE INVENTION

1. Introduction

Figure 1:
FIGS. 1A-1C. Formation of circularized MIP product in routine MIP assays, and the new ligated and linear MIP (LL-MIP) products used in the present invention.

The present invention provides methods and compositions for determining the length of a tandem repeat by quantification of the abundance of the corresponding repeat motif in a sample. One particular type of tandem repeat of interest here is the telomere. The methods and compositions involve the use of molecular inversion probes (MIPs) that are specifically designed for use on tandem repeat sequences.

The present methods and compositions provide MIPs that are specifically designed for tandem repeat-containing regions of the genome and take advantage of the multiplicity of ligation products that are generated in MIP-based assays on such regions, including both circularized and ligated linear products. The methods quantify the circularized and ligated linear products to allow reliable and rapid assessments of the copy number of tandem repeat sequences that vary between individuals, such as telomere sequences. In particular, in preferred methods the invention involves the use of MIPs directed to tandem repeat sequences where the 5' and 3' ends of the MIPs comprise the same sequence, where they are typically 100% complementary to the template DNA sequence, and where they are designed to be able to bind to a template DNA strand with a small gap between the 3' and 5' ends of the MIP of a small number of nucleotides, e.g., 1-3 nucleotides, when bound within a single repeat unit on a template DNA. Further, the gap between of 3' and 5' ends of the present MIPs typically comprise only 1 or 2 different nucleotides, allowing the use of one or two dNTPs in the methods and thereby ensuring that ligation of the ends can only occur within a single repeat unit of the tandem repeat, and not across multiple repeats. In preferred embodiments, the methods omit steps, e.g., exonuclease-based steps, to remove linear products prior to detection and/or quantification, and instead quantify ligation points of both circularized and ligated linear products in order to determine the abundance of the specific repeat motif in a sample as an indicator parameter of telomere length or of the length of another genomic motif.

2. Definitions

As used herein, the term "about" with respect to the size of, e.g., a polynucleotide, to percent homology, or to any other quantitative measure means that a small degree of variation is possible in the value provided. For example, "about" means that the value can vary by, e.g., +/−1%, 2%, 3%, 4%, 5%, 6%, 7%, 8%, 9%, or 10% from the stated value.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al.,Nucleic Acid Res. 19:5081 (1991); Ohtsuka et al., J. Biol. Chem. 260:2605-2608 (1985); and Rossolini et al., Mol. Cell. Probes 8:91-98 (1994)).

A "molecular inversion probe" (MIP) is a nucleic acid probe that hybridizes to complementary sequences of a target nucleic acid of interest with the MIP 5' end hybridizing 5' on the target from the position at which the MIP 3' end hybridizes to the target, i.e. when the 5' and 3' ends are bound adjacently within a single repeat. When hybridized to a target, MIPs form a loop back from one end to the other, such that the ends are "inverted" relative to one another, i.e. the 3' end is located 5' of the 5' end of the MW. The MIP sequences located at the two ends of the MW are configured to hybridize to target sequences and are referred to herein as the 5' and 3' homology regions. Between the 5' and 3' homology regions is a linker region that is not substantially complementary to the target DNA sequence and thus does not hybridize to the template DNA, and which contains one or more functional elements such as primer binding sites, tag sequences, etc. Typically, 5' phosphorylation is required for MIP to enable ligation to proceed.

To "circularize", as used herein, refers to ligating a 3' end of a nucleic acid to a 5' end of the nucleic acid, thereby creating a continuous uncut loop or circle. A "ligated linear MIP" or "LL-MIP" or "ligated linear probe" refers to two or more MIPs that have been ligated to one another, i.e. the 3' terminus of one MIP has been extended (through "gap filling") and ligated to the 5' terminus of a different MIP that is bound adjacently, e.g., just 3' within a single repeat unit on the template, to the same DNA template.

The term "complementary" as used herein refers to the hybridization or Watson-Crick base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary.

See, M. Kanehisa Nucleic Acids Res. 12:203 (1984). Typically, with homology regions of a MIP there is 100% complementarity with target nucleic acid of interest, although mismatches may be included in certain embodiments.

"Gap-filling" is a reaction, described herein, in which a gap is filled by the action of a polymerase between 5' and 3' ends of a molecular inversion probe hybridized to a complementary target nucleic acid. Gap filling is also referred to herein as "extension" of the 3' end of a bound MIP probe, where the extension covers the gap and allows ligation between the extended 3' end and the bound 5' end. In preferred embodiments, the filled gap consists of 1-3 nucleotides or is confined to within a single repeat motif unit.

"Homology regions", e.g., "3' homology regions" or 5' homology regions", as used herein are those parts of a molecular inversion probe that are complementary to the target nucleic acid of interest. MIPs typically have two homology regions (HRs), one at or near the 5' end of the probe and one at or near the 3' end. In preferred embodiments, the HRs of the invention are adapted to be able to hybridize to a tandem-repeat containing target nucleic acid of interest so that they are separated by a gap of a 1-3 nucleotides within a single repeat unit on the target DNA sequence. In preferred embodiments, the homology regions are 100% complementary to the target sequence, but in some embodiments mismatches can be present, e.g., 1, 2, 3 or more mismatches in a given homology region.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." Hybridizations are usually performed under stringent conditions, for example, at a salt concentration of no more than about 1 M and a temperature of at least 25° C. Hybridizations may be performed in the presence of agents such as herring sperm DNA at about 0.1 mg/ml, or (acetylated) BSA at about 0.5 mg/ml. As other factors may affect the stringency of hybridization, including base composition and length of the complementary strands, the combination of parameters is more important than the absolute measure of any one alone. Additional guidance for hybridization conditions suitable for various assays can be found, e.g., in Michael R. Green & Joseph Sambrook, Molecular Cloning: A Laboratory Manual, (4th ed. 2012).

"Polymerase chain reaction," or "PCR," means a reaction for the in vitro amplification of specific DNA sequences by the simultaneous primer extension of complementary strands of DNA, as is well known in the art. PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999) (two-color real-time PCR). Usually, distinct sets of primers are employed for each sequence being amplified. "Quantitative PCR" or "qPCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989).

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, a DNA polymerase, RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable specific hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

"Sample" means a quantity of material from a biological, environmental, medical, animal, bacterial, plant or patient source in which detection or measurement of target nucleic acids is sought. Often a sample is a lysate of an organism tissue of cells. Typically, samples in the present context include materials comprising nucleic acids. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Biological samples may also be obtained from plants, such as maize, rice, wheat, lettuce and pepper.

The term "target nucleic acid of interest", as used herein, refers to the sample nucleic acid putatively including a target sequence of interest, e.g., a tandem repeat-containing region such as a telomere or ATGG-containing region of the genome. The target sequence of interest, with regard to a MIP, includes those sequences complementary to the MIP homology regions.

A tandem repeat refers to a nucleotide sequence in which a short nucleotide sequence unit of 2-60 nucleotides long is repeated multiple times where the repeated units are directly adjacent to one another. The exact nucleotide sequence of each repeat unit is called the repeat motif. Common examples of repeat motifs, also referred to herein as repeating units, include [CA], [CAG], [GATA], etc. Tandem repeats are classified into microsatellites and minisatellites depending on the length of repeat motif. Typically, the repeat motif units of microsatellites are short and less than 10 nucleotides. Dinucleotide repeats (e.g. $[CA]_n$ repeats) are one of the best known microsatellites or short tandem repeats in the human genome. The length of repeat motif in minisatellites ranges from 10 to 60 nucleotides. As one example, the repeat motif in the human telomere, [TTAGGG], can be repeated hundreds or thousands of times within the telomeres at the end of each chromosome. [TTAGGG] is thus the sequence motif specific for the human telomere repeat, and [TTAGGG]n is used to represent the repeating nature of the motif in the telomere. It will be understood that tandem repeat sequences can refer to either or both strands of the DNA containing the tandem repeat. Tandem repeats can be variable in the genome, such as with telomeres, meaning that the number of repeated units, or copy number, or the overall size of the region of the genome carrying the repeats, can vary by any degree, e.g., 1.1, 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10 fold or greater between individuals, or between different cells or cell types in an individual. Tandem repeats can also be "stable," or relatively "constant" in the genome, such as with the ATGG repeat, e.g., meaning that the number of repeated units, or copy number, or the overall size of the region of the genome carrying the repeats, does not vary by more than, e.g., 1%, 2%, 3%, 4%, 5%, 6%, 7%, 8%, 9%, 10%, 15%, 20%, 25%, 30%, or more between individuals or between different cells or cell types in an individual.

A "hybridizing condition" is a condition expected to result in specific hybridization between complementary sequences, e.g., a test nucleic acid is said to specifically hybridize to a probe nucleic acid when it hybridizes at least 50% as well (e.g., quantitatively under the same hybridization conditions) to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5x-10x as high as that observed for hybridization to any of the unmatched target nucleic acids.

As used in herein, the terms "identical" or percent "identity," in the context of describing two or more polynucleotide sequences, refer to two or more sequences or specified subsequences that are the same. Two sequences that are "substantially identical" have at least 60% identity, preferably 65%, 70%, 75%, 80%, 85%, 90%, 91%, 92%, 93, 94%, 95%, 96%, 97%, 98%, 99%, or 100% identity, when compared and aligned for maximum correspondence over a comparison window, or designated region as measured using a sequence comparison algorithm or by manual alignment and visual inspection where a specific region is not designated. With regard to polynucleotide sequences, this definition also refers to the complement of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST 2.0 algorithm and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned.

An algorithm for determining percent sequence identity and sequence similarity is the BLAST 2.0 algorithm, which is described in Altschul et al., (1990) J. Mol. Biol. 215: 403-410. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands (see Henikoff & Henikoff, Proc. Natl. Acad. Sci. USA 89:10915 (1989)).

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

3. Tandem-Repeat Targeting Molecular Inversion Probes

The MIPs of the invention are single-stranded DNA probes comprising three regions: a 5' homology region located in the 5' portion of the MIP, a 3' homology region located in the 3' portion of the MIP, and a central linker region located between the 5' and 3' homology regions. As described in more detail below, the 5' and 3' homology regions are designed to be homologous to the same strand of the template DNA comprising the tandem repeat sequence, such that the 3' end can bind to the template adjacent, i.e., just in the 3' direction on the template DNA, to the 5' end, allowing the 3' end to be extended by DNA polymerase and ligated to the adjacent 5' end. It will be appreciated, however, that due to the nature of the repeated sequence within the template DNA, the 5' and 3' ends are capable of binding to any repeat unit within the tandem repeat, and can therefore be separated by multiple repeat units when bound. The linker region, in contrast, loops between the hybridized 3' and 5' homology regions and does not bind to the template DNA. It will be appreciated that any of the MIP sequences, MIP sequence targets, homology regions, linker sequences, etc. disclosed herein, including in the Examples and in the Sequence Listing, can be used in any of the present methods and compositions, as can any of the primers and other sequences disclosed herein.

The homology regions are typically 15-25 nucleotides in length, e.g., 18-22 nucleotides in length, and are typically 100% complementary to the tandem repeat sequence within the template (i.e., they are 100% identical to the non-hybridized strand of the template DNA), although homology regions that are less than 100% complementary, e.g., that are 90%, 95%, 96%, 97%, 98%, or 99% complementary, or that contain, e.g., 1, 2, 3 or more mismatches, can also be used. The 5' and 3' regions typically extend to the respective termini of the MIP, i.e. the 5' end of the 5' homology region is also the 5' end of the MW, and the 3' end of the 3' homology region is also be the 3' end of the MIP. In cases where there is less than 100% complementary to the template tandem repeat sequence, the mismatched nucleotides typically do not include the terminal 5' and 3' nucleotides of the MIP (i.e., the terminal nucleotides that will be extended by DNA polymerase and/or ligated in the present methods). In contrast to other assays, e.g., the real time PCR telomere T/S ratio assay, the hybridization sequences in the 5' and 3' ends of the present MIPs are preferably 100% identical to a segment of telomere repeat motif [TTAGGG], with no mismatched bases.

The central linker region can be of varying size, but will typically be about 30-200 nucleotides in length, e.g., 30, 35, 40, 45, 50, 55, 60, 65, 70, 75, 80, 85, 90, 95, 100, 110, 120, 130, 140, 150, 160, 170, 180, 190, or 200 nucleotides in length, or a number corresponding to any integer within this range, and in addition to being of sufficient length to allow the 5' and 3' homology regions to form a loop in order to bind to the same template DNA, can contain any of a number of functional sequences for, e.g., the isolation, purification, detection, cleavage, or quantification of the products of the presently described methods. For example, the linker region can contain universal primer sequences, MW-specific primer sequences, probe sequences, e.g., TaqMan probe sequences, tag ID or barcode sequences, and restriction enzyme recognition or cleavage sites.

Tandem Repeat Sequences and Homology Regions

The present compositions and methods can be used to detect the copy number or length of any tandem-repeat sequence containing region of the genome, including regions whose overall length or size, i.e., the copy number of the repeat, varies between individuals, such as a telomere. Any such sequence can be assessed using the present methods and compositions. In numerous embodiments, the methods and compositions are used to determine the precise or approximate copy number, i.e., the overall length, of a telomere, e.g., a human telomere. In numerous embodiments, a tandem repeat whose size or copy number does not substantially vary between individuals and is thus said to be "stable" or "constant", e.g., the 4-bp short tandem repeat [ATGG] sequence within the human genome, is also assessed.

Tandem repeats can be analyzed regardless of the length of the individual repeat unit and regardless of the number of copies of the tandem repeat in the genome. For example, the 6-nucleotide human telomere sequence (TTAGGG) can be repeated hundreds or thousands of times, covering, e.g., from 1-11 kb within the genome, but it is also possible to assess the copy number of tandem repeat sequences that are repeated fewer times than this, e.g., tens to hundreds of repeats in the genome, or that are repeated greater times than this, e.g., tens or hundreds of thousands of times in the genome.

The present methods can be used to assess the overall length of a telomere or other tandem repeat region in an individual, e.g., to assess on a one-time basis whether the telomere is longer or shorter than a standard reference length, e.g., to determine whether it indicates the presence or absence of a condition associated with altered telomere length, and they can also be used to assess the evolution of the telomere or other tandem repeat region in a single individual, e.g., to assess the efficacy of a therapeutic regimen with respect to its effect on, e.g., telomere length.

The length of the individual repeated sequence unit within the tandem repeats assessed using the present methods can be of any size, e.g., from 2-20 nucleotides, e.g., 2, 3, 4, 5, 6, 7, 8, 9, 10, 11, 12, 13, 14, 15, 16, 17, 18, 19, 20 nucleotides or more. In some embodiments, the repeated sequence is 6 nucleotides, such as in human telomeres, or 4 nucleotides, such as in the human ATGG repeat or AAGG repeat. In certain embodiments, repeats that are expanded in conjunction with certain disease states, e.g., the CGG triplet repeat that is expanded with the Fragile-X syndrome, or the CAG triplet repeat expanded with Huntington's disease, are assessed.

In addition to assessing variable tandem repeats such as telomeres, the methods and compositions can also be used to assess the length or copy number of repeated sequences that are relatively constant or stable between individuals, e.g., for use as an internal control when assessing the size of a variable region, e.g., telomere, in a genome. The size of such constant sequences will preferably vary by, e.g., less than 50%, 40%, 30%, 20%, 10%, 5%, 4%, 3%, 2%, 1% or less between individuals on average, or the relative level between individuals will not vary by more than, e.g., 0.5, 0.6, 0.7, 0.8, 0.9, 1, 1.1, 1.2, 1.3, 1.4, 1.5, 1.6, 1.7, 1.8, 1.9, or 2 fold on average. In some embodiments, the constant sequences used in the present methods are present in large copy numbers in the genome, e.g., comprising hundreds or thousands of tandem repeats, such that they are present at similar levels as the variable repeat sequence, e.g., telomere. This use of high copy number control sequences provides a significant advantage over traditional methods of assessing tandem repeats, e.g., telomere length, which have tended to use non-repeated sequences as controls.

For both variable and constant repeats, the methods can be used to assess the overall size of the repeat-containing region of the genome, e.g., the length of the region to an accuracy of, e.g., 50%, 55%, 60%, 65%, 70%, 75% 80%, 85%, 90%, 95%, 96%, 97%, 98%, 99%, or more, or the approximate or precise number of repeats to an accuracy of, e.g., 50%, 55%, 60%, 65%, 70%, 75%, 80%, 85%, 90%, 95%, 96%, 97%, 98%, 99%, or more.

In one embodiment, the sequence ATGG is used as a constant, control repeated sequence. Other tandem repeats that be used include, inter alfa, AAGG, GAATG, AATGG, ACTCC, CAGC, AACGG, AACAT, ACAGAG, AGGGTC, AAAAT, AAAAG, GAGAGG and AACC. Any of a number of tandem repeats can be used, provided that their quantity is relatively stable in the genomes of individuals of the species under investigation, e.g. in humans when human telomere length is being assessed, and that appropriate MIPs can be designed for targeting the tandem repeat using methods as described herein.

5' and 3' Homology Regions

The 5' and 3' homology regions of the MIPs comprise nucleotide sequences that are homologous to tandem repeat sequences within the template DNA. In preferred embodiments, the 5' and 3' regions are 100% homologous to the tandem repeat sequences, although in some embodiments the 5' and/or 3' region can contain mismatches, e.g., 1, 2, 3 or more mismatches within a given homology region with respect to the tandem repeat sequence. The 5' homology region begins at the 5' terminus of the MIP and extends, e.g., 15-25 nucleotides into the MIP, and the 3' homology region begins at the 3' terminus of the MIP and extends, e.g., 15-25 nucleotides into the MW. The 5' and 3' homology regions are complementary to the same strand of the template DNA, i.e., they both comprise the same repeated sequence, e.g., comprising 2, 3, 4, 5, 6, or more repeat units (e.g., an 18-base-pair homology region targeting the human telomere would contain 3 of the 6-base-bair repeats). The 5' and 3' regions are designed such that the 3' homology region can bind to the template just 5' of the 5' homology region within the same repeat unit on the template, but separated by a small number of nucleotides on the template, e.g., 1-3 nucleotides, such that ligation can only take place following the extension of the 3' end (i.e., "gap filling") with DNA polymerase to add the 1-3 nucleotides within the gap.

One important consideration when designing MIPs for use in the present invention, and in particular the 5' and 3' homology regions, is the gap that separates the 5' and 3' ends of the MW when the two ends hybridize adjacent to one another within a single repeat unit on the same DNA template. Typically, for use in the present methods, the 5' and 3' ends of the MIP will be separated by a small number of nucleotides, e.g., 1, 2, or 3 nucleotides. It will be appreciated that the size of the gap between the 5' and 3' ends of the MIP can differ between the different MIPs used in a given assay, i.e., the MIP used to assess the copy number of a variable tandem repeat sequence such as a telomere could be, e.g., 1, 2, or 3 nucleotides, and the control MIP used to assess the copy number of a constant tandem repeat sequence such as ATGG could be, e.g., 1, 2, or 3 nucleotides, with the number of nucleotides in the two gaps being independent of one another.

It will be appreciated that the 5' and 3' homology regions can be designed to hybridize to either strand of the template DNA, so long as both regions share the same sequence, i.e. such that they both target the same strand.

An additional consideration to that of the number of nucleotides separating the 3' and 5' ends of a MIP when bound within a single repeat unit of a template DNA strand is the identity of the bases corresponding to the nucleotides within the gap. In preferred embodiments in the design of the telomere-targeting MIPs, regardless of the number of nucleotides within the gap, the nucleotides will comprise one or two bases, such that the extension step of the present methods can be performed in the presence of only those deoxyribonucleoside triphosphates (dNTPs) corresponding to the one or two bases within the gap. In this way, as illustrated below, the one or two dNTPs present in the reaction mixture are sufficient to allow extension across a gap within a single given repeat unit, but are insufficient to permit extension across multiple repeat units, where, e.g., three or four dNTPs would be required.

For illustration purposes, as the human telomere sequence motif is GGGTTA, the template (complementary) DNA strand for an MIP targeting this sequence would be in 3' to 5' direction) 3'-[AATCCC]$_n$-5' or 3'- . . . . CCCAATCC-CAATCCCAAT-5' (SEQ ID NO: 31) . . . representing a segment that is 3 motifs in length. Accordingly, the 5' end of a MIP targeting this sequence could read 5'-GTTAGGGT-TAGGGTTAGGGTT- (SEQ ID NO: 32) and the 3' end could read -TAGGGTTAGGGTTAGGGTTA-3' (SEQ ID NO: 7). In this way, if the two ends bind adjacently to the same template, i.e., with the 3' end just 3' of the 5' end within a single repeat, the G at the 5' end of the probe could hybridize up to the last (the sixth base) C in an AATCCC repeat motif on the template, and the A at the 3' end of the probe could hybridize adjacently, down to the T (the third base) within the same repeat (i.e., from left to right, ending on the third nucleotide within AATCCC). As such, the two ends would be separated by the first two Cs (the fourth and fifth bases) in the motif, and could thus be joined together if a DNA polymerase adds two Gs to the 3' end of the MIP, and if the second added G is then ligated to the G at the 5' end of the MIP. In this case, where the two ends belong to the same MIP, the MIP would be circularized. Alternatively, if the two ends belong to different MIPs, a ligated linear MIP would be produced, comprising two MIPs ligated to one another.

Similarly, for the human ATGG 4-base pair repeat, which can be used as a control MIP to assess the copy number of a constant or stable repeat sequence in the genome, the template would be (in 3' to 5' direction) 3'-[CCTA]$_n$-5' or 3'- . . . . TACCTACCTACC-5' (SEQ ID NO: 33) . . . . In this case, the 5' end of the MIP could be 5'-ATGGATGGATG-GATGGATGGATGG-(SEQ ID NO: 34), and the 3' end of the MIP could be GGATGGATGGATGGATGGAT-3' (SEQ ID NO: 35). Accordingly, if the two ends bound adjacently to the same template, the A at the 5' end could hybridize up to a T in one of the repeat units within the template (i.e., from right to left, up to the seventh nucleotide in CCTACCTA), and the T at the 3' end could hybridize down to an A within the template (i.e., from left to right, up to the fourth nucleotide within CCTACCTA). In this case as well, the two ends of the MIP would be separated by the two Cs within a single repeat, and could thus be linked if a DNA polymerase adds two Gs to the 3' end of the MIP, and if the second G is then ligated to the A at the adjacent 5' end.

Similarly, for the human ATGG 4-base pair repeat, which can be used as a control MW to assess the copy number of a constant or stable repeat sequence in the genome, the template would be [CCTA]$_n$ or . . . TACCTACCTACC . . . In this case, the 5' end of the MIP could be 5'-ATGGATG-GATGGATGGATGGATGG-, and the 3' end of the MIP could be GGATGGATGGATGGATGGAT-3'. Accordingly, if the two ends bound adjacently to the same template, the A at the 5' end could hybridize up to a T in one of the repeat units within the template (i.e., from right to left, up to the seventh nucleotide in CCTACCTA), and the T at the 3' end could hybridize down to an A within the template (i.e., from left to right, up to the fourth nucleotide within CCTACCTA). In this case as well, the two ends of the MIP would be separated by the two Cs within a single repeat, and could thus be linked if a DNA polymerase adds two Gs to the 3' end of the MIP, and if the second G is then ligated to the A at the adjacent 5' end.

In the two above examples, i.e., with the MIP targeting the human telomere sequence and the MIP targeting the ATGG repeat, all of the nucleotides within the gaps between the 3' and 5' ends of the two MIPs within a single repeat comprise the base C on the template. In this way, a DNA-polymerase-mediated extension of the 3' ends of the MIPs could take place in the sole presence of dGTP, but with no other dNTPs present in the reaction mixture. As this is the case with both of the MIPs, a multiplex reaction can be performed in which the two MIPs are used simultaneously in the same reaction, with the same genomic DNA template. Further, if only dGTP is used, this also means that extension can only take place within a single repeat, and that extension across multiple repeats, i.e. if the 3' and 5' ends are bound to the template more than one repeat unit apart from one another, would not be possible, as this would require not only dGTP but also dATP and dTTP. For this reason, in numerous embodiments of the present methods and compositions, only one or two dNTPs are used or included.

In one embodiment, the only dNTP included in the reaction in dGTP. In other embodiments, the only two nucleotides included are dGTP and dATP. It will be understood, however, that the MIPs can be designed such that any combination of one or two dNTPs can be used, as long as the dNTP or dNTPs used allow extension within, but not across, the tandem repeat units of the telomere targeting MIP.

Linker Region

The linker region is located between the 5' and 3' homology regions, does not hybridize to, i.e, is not complementary to, the template DNA, and it provides both a spacer function that allows the probe to take on a circular (loop) conformation when the 5' and 3' homology regions bind to the same template DNA, and also comprises any of a number of elements that allow, e.g., the identification, isolation, cleavage, or amplification of the probe. Examples of such sequence elements include primer binding sites that are common to all the MIPs used in a given assay, e.g., common forward primer binding sites; probe-specific primer binding sites, e.g., reverse primer binding sites that are specific to each MIP; probe-binding sequences, e.g., sequences bound by probes for quantitative amplification reactions such as TaqMan probes; tag or barcode sequences; and cleavage or restriction sites that can be used, e.g., to linearize the circularized MIPs prior to amplification reactions.

The linker region can be of any size, e.g., 20, 25, 30, 35, 40, 45, 50, 55, 60, 65, 70, 75, 80, 85, 90, 95, 100, 110, 120, 130, 140, 150, 160, 170, 180, 190, 200, or more nucleotides, and can include any number of elements, e.g., 1, 2, 3, 4, 5, 6, 7, 8, 9, 10 or more elements.

The tag sequences or barcodes that can be included in the linker region are unique sequences that can encode any desired information, e.g., a sample identification sequence, target information sequence, sample acquisition time encoding sequence, etc., allowing their identification by, e.g., by sequencing or hybridization properties. With the inclusion of such sequences, MIP products from multiple samples can be unambiguously detected in a single detection event. The tag elements can include information, such as within a "barcoded" nucleic acid sequence, which is readable by, e.g., a sequencing procedure or specific hybridization. Alternately, the one or more tag elements can be an affinity moiety that can specifically bind the MIP to an identifiable array location. For instance, the tag can be interrogated by a nucleic acid array having polynucleotide probes that are complementary to the various tag sequences. For example, the tag can include a sequence complementary to a capture probe of a branched DNA (bDNA) procedure. bDNA capture probes can be laid out in an array on a solid support with each location corresponding to a particular tag and sample. Optionally, the tag could correspond with a bead having appropriate capture and signaling elements, e.g., for detection in a FACS flow device or by imaging with a charge coupled device.

Cleavage sites can be introduced, e.g., by incorporating any of a number of modified nucleotides or bases into the linker region at the desired site for cleavage, and/or through the configuration of the linker to be cleaved by, e.g., uracil N-glycosylase, or by other appropriate enzymes known to those of ordinary skill in the art, e.g. restriction enzymes.

Other nucleic acid derivatives may also be incorporated into the MIPs of the invention, for example to prevent their digestion, particularly when they are exposed to biological samples that may contain nucleases. As used herein, a nucleic acid derivative is a non-naturally occurring nucleic acid or a unit thereof. Nucleic acid derivatives may contain non-naturally occurring elements such as non-naturally occurring nucleotides and non-naturally occurring backbone linkages.

Nucleic acid derivatives may contain backbone modifications such as but not limited to phosphorothioate linkages, phosphodiester modified nucleic acids, phosphorothiolate modifications, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof. The backbone composition of the nucleic acids may be homogeneous or heterogeneous.

Nucleic acid derivatives may contain substitutions or modifications in the sugars and/or bases. For example, they may include nucleic acids having backbone sugars which are covalently attached to low molecular weight organic groups other than a hydroxyl group at the 3' position and other than a phosphate group at the 5' position (e.g., an 2'-0-alkylated ribose group). Nucleic acid derivatives may include non-ribose sugars such as arabinose. Nucleic acid derivatives may contain substituted purines and pyrimidines such as C-5 propyne modified bases, 5-methylcytosine, 2-aminopurine, 2-amino-6-chloropurine, 2,6-diaminopurine, hypoxanthine, 2-thiouracil and pseudoisocytosine. In some embodiments, substitution(s) may include one or more substitutions/modifications in the sugars/bases, groups attached to the base, including biotin, fluorescent groups (fluorescein, cyanine, rhodamine, etc.), chemically-reactive groups including carboxyl, NHS, thiol, etc., or any combination thereof.

In some embodiments, other methods are used to enhance the formation of LL-MIP products, such as through the use of locked nucleic acid bases in the linker region of the MIP to pre-form an internal self-loop. Locked nucleic acids (LNA) contain one or more nucleotide building blocks in which an extra methylene bridge fixes the ribose moiety either in the C3'-endo (beta-D-LNA) or C2'-endo (alpha-L-LNA) conformation. LNAs can be synthesized using commercial nucleic acid synthesizers and standard phosphoramidite chemistry.

4. Biological Samples and Isolation of Genomic DNA

To carry out the present methods, one or more MIP probes are hybridized, e.g., in a multiplex reaction, to a biological sample containing genomic DNA from an individual for which it is desired to determine the length, e.g., approximate or precise copy number, of a tandem repeat region such as the telomere. In some embodiments, samples are taken from individuals with characteristics, lifestyle factors, or conditions that have been associated with altered telomere size, e.g., telomere loss, such as aging and various aging-related conditions, cognitive decline, mental disorders such as depression, schizophrenia, stress-anxiety, cancer, cardiovascular diseases, diabetes, and various lifestyle factors such as diet, smoking, physical activity, and alcohol intake. The methods could be performed in such individuals, or in individuals thought to be susceptible to such characteristics, factors, or conditions, for, e.g., screening purposes or diagnostic purposes (i.e., in a one-time assessment in which the telomere length is compared to a reference telomere length), or to monitor a reaction to a given therapeutic protocol (i.e., in which the telomeres of a given individual are measured repeatedly over time to monitor their evolution).

Any source of genomic DNA can be used in the present invention, such as genomic DNA from peripheral blood cells. Other cell types can be used as well, for example in specific cell types, e.g., cancer cells, to monitor telomere length in the particular cell type. Suitable samples include, but are not limited to: biological samples, such as tissue and bodily fluid. For example, samples are obtained from, e.g., blood, urine, serum, lymph, saliva, anal and vaginal secretions, perspiration and semen, skin, organs and the like.

The isolation of target nucleic acid is obtained from a sample using methods known in the art. Isolating nucleic acid from a biological sample generally includes treating a biological sample in such a manner that genomic nucleic acids present in the sample are extracted and made available for analysis. Any isolation method that results in extracted/isolated genomic nucleic acid may be used in the practice of the present invention.

Generally, nucleic acids are extracted using techniques such as those described in Sambrook, J., Fritsch, E R, and Maniatis, T. (1980)) Molecular Cloning: A Laboratory Manual. 2nd ed. Cold Spring Harbor, N.Y.:Cold Spring Harbor Laboratory.). Other methods include: salting out DNA extraction (P. Sunnucks et al., Genetics, 1996, 144: 747-756; S. M. Aljanabi and I. Martinez, Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). Several protocols have been developed to extract genomic DNA from blood.

There are also numerous kits that can be used to extract DNA from tissues and bodily fluids and that are commercially available from, for example, BD Biosciences Clontech (Palo Alto, Calif.), Epicentre Technologies (Madison, Wis.), Gentra Systems, Inc. (Minneapolis, Minn.), MicroProbe Corp. (Bothell, Wash.), Organon Teknika (Durham, N.C.), Qiagen Inc. (Valencia, Calif.), Autogen (Holliston, Mass.); Beckman Coulter (Brea, Calif.), (AutoGenFlex STAR robot with Qiagen FlexiGene chemistry. For example, Autogen manufactures FlexStar automated extraction kits used in combination with Qiagen FlexiGene Chemistry, and Beckeman Coulter manufactures Agencourt GenFind kits for bead-based extraction chemistry. User Guides that describe in detail the protocol(s) to be followed are usually included in all these kits, for example, Qiagen's literature for their PureGene extraction chemistry entitled "Qiagen PureGene Handbook" 3rd Edition, dated June 2011.

After cells have been obtained from the sample, it is preferable to lyse cells in order to isolate genomic nucleic acid. Cellular extracts can be subjected to other steps to drive nucleic acid isolation toward completion by, e.g., differential precipitation, column chromatography, extraction with organic solvents and the like. Extracts then may be further treated, for example, by filtration and/or centrifugation and/or with chaotropic salts such as guanidinium isothiocyanate or urea or with organic solvents such as phenol and/or HCC13 to denature any contaminating and potentially interfering proteins. The genomic nucleic acid can also be resuspended in a hydrating solution, such as an aqueous buffer. The genomic nucleic acid can be suspended in, for example, water, Tris buffers, or other buffers. In certain embodiments the genomic nucleic acid can be re-suspended in Qiagen DNA hydration solution, or other Tris-based buffer of a pH of around 7.5.

Depending on the type of method used for extraction, the genomic nucleic acid obtained can vary in size. The integrity and size of genomic nucleic acid can be determined by, e.g., pulse-field gel electrophoresis (PFGE) using an agarose gel.

In some embodiments, the genomic DNA will be fragmented prior to use in the present methods. Nucleic acids, including genomic nucleic acids, can be fragmented using any of a variety of methods, such as mechanical fragmenting, chemical fragmenting, and enzymatic fragmenting. Methods of nucleic acid fragmentation are known in the art and include, but are not limited to, DNase digestion, sonication, mechanical shearing, and the like (J. Sambrook et al., "Molecular Cloning: A Laboratory Manual", 1989, 2. sup.nd Ed., Cold Spring Harbour Laboratory Press: New York, N.Y.; P. Tijssen, "Hybridization with Nucleic Acid Probes—Laboratory Techniques in Biochemistry and Molecular Biology (Parts I and II)", 1993, Elsevier; C. P. Ordahl et al., Nucleic Acids Res., 1976, 3: 2985-2999; P. J. Oefner et al., Nucleic Acids Res., 1996, 24: 3879-3889; Y. R. Thorstenson et al., Genome Res., 1998, 8: 848-855). U.S. Patent Publication 2005/0112590 provides a general overview of various methods of fragmenting known in the art.

In numerous embodiments, the genomic DNA is digested with a restriction enzyme, e.g., an enzyme with a restriction site that is not found within any of the sequences targeted by the MIPs used in the assay. Restriction endonucleases recognize specific sequences within double-stranded nucleic acids and generally cleave both strands either within or close to the recognition site in order to fragment the nucleic acid. Naturally occurring restriction endonucleases are categorized into four groups (Types I, II III, and IV) based on their composition and enzyme cofactor requirements, the nature of their target sequence, and the position of their DNA cleavage site relative to the target sequence. Bickle T A, Kruger D H (June 1993). "Biology of DNA restriction". Microbiol. Rev. 57 (2): 434-50; Boyer H W (1971). "DNA restriction and modification mechanisms in bacteria". Annu. Rev. Microbiol. 25: 153-76; Yuan R (1981). "Structure and mechanism of multifunctional restriction endonucleases". Annu. Rev. Biochem. 50: 285-319. All types of enzymes recognize specific short DNA sequences and carry out the endonucleolytic cleavage of DNA to give specific fragments with terminal 5'-phosphates. The enzymes differ in their recognition sequence, subunit composition, cleavage position, and cofactor requirements. Williams RJ (2003). "Restriction endonucleases: classification, properties, and applications". Mol. Biotechnol. 23 (3): 225-43.

In one embodiment, the DNA is digested with AluI (e.g., from New England Biolabs), e.g., 50 ng of DNA is digested with 10 units of AluI for at 37° C. for 2 hours, prior to inactivation of the enzyme (e.g, by incubating at 90° C. for 20 minutes) and centrifugation of the DNA (e.g., at 7k rpm for 10 minutes) and collection of the supernatant. The DNA can then be stored, e.g, at 4° C., until use in the present methods.

In another embodiment of the invention, the present methods and compositions can be used to assess, i.e., quantify, the extent of methylation at a genomic scale. For example, in the DNA sample pre-digestion step, a methylation sensitive restriction enzyme can be added to the pre-digestion of DNA sample. The results of two reactions from the same sample are then compared, namely in the presence of a methylation sensitive restriction enzyme (whose ability to cut DNA depends on the presence of methylated nucleotides) and in the presence of a methylation insensitive restriction enzyme that recognizes the same restriction site (isoschizomers). For example, the pair of enzymes HpaII (methylation sensitive) and MspI can be used. For such methods, additional MIPs designed to target CpG islands can be used together with a genomic reference MIP such as the 4-base pair (ATGG) MIP described herein.

In some embodiments, the present methods also provide for denaturing the genomic DNA to render it single stranded for hybridization to the present MIP probes. Denaturation can result from the fragmentation method chosen, as described above. For example, one skilled in the art will recognize that a genomic nucleic acid can be denatured during pH-based shearing or fragmenting via nicking endonucleases. Denaturation can occur either before, during, or after fragmentation. In addition, the use of pH or heat during the fragmenting step can result in denatured nucleic acid fragments. See, for example, McDonnell, "Antisepsis, disinfection, and sterilization: types, action, and resistance," pg. 239 (2007).

Heat-based denaturing is the process by which double-stranded deoxyribonucleic acid unwinds and separates into single-stranded strands through the breaking of hydrogen bonding between the bases. Heat denaturation of a nucleic acid of an unknown sequence typically uses a temperature high enough to ensure denaturation of even nucleic acids having a very high GC content, e.g., 95-98° C. in the absence of any chemical denaturant. It is well within the abilities of one of ordinary skill in the art to optimize the conditions (e.g., time, temperature, etc.) for denaturation of the nucleic acid.

Denaturing nucleic acids with the use of pH is also well known in the art, and such denaturation can be accomplished using any method known in the art such as introducing a nucleic acid to high or low pH, low ionic strength, and/or heat, which disrupts base-pairing causing a double-stranded helix to dissociate into single strands. For methods of pH-based denaturation see, for example, Dore et al. Biophys J. 1969 November; 9(11): 1281-1311; A. M. Michelson The Chemistry of Nucleosides and Nucleotides, Academic Press, London and New York (1963). Nucleic acids can also be denatured via electro-chemical means, for example, by applying a voltage to a nucleic acid within a solution by means of an electrode.

Hybridization, Extension, and Ligation

It will be appreciated that aspects of the invention can involve varying the amounts of genomic nucleic acid and varying the amounts of MIP probes to reach a customized result. In some embodiments, the amount of genomic nucleic acid used per subject ranges from 1 ng to 10 µg (e.g., 500 ng to 5 µg). However, higher or lower amounts (e.g., less than 1 ng, more than 10 µg, 10-50 µg, 50-100 µg or more) may be used. In some embodiments, for each tandem repeat of interest, the amount of probe used per assay may be optimized for a particular application. In some embodiments, the ratio (molar ratio, for example measured as a concentration ratio) of MIP probe to genome equivalent (e.g., diploid genome equivalent) ranges from $1 \times 10^6$ to $1 \times 10^{12}$ or 1e6 to 1e12. However, lower, higher, or intermediate ratios may be used, in particular as a function of the abundance of the repeat motif per genome.

In the present methods, to insure maximum coverage of each repeat within a repeat array such as at a telomere, the MIPs will typically be present in an excess relative to the genomic DNA. The ratios of MIP probe to genome equivalent mentioned above are higher than those used in conventional MIP assays. For example, the ratios are up to 1000× or higher than in traditional MW methods, so as to saturate the potential binding sites within the genome, e.g. the repeat sequences, and maximize the number of ligated products generated, whether circular products or ligated linear products. In one embodiment, 50 ng of genomic DNA is used (e.g., 5 µl of a 10 ng/µl solution) and 2 µl of a 10 nM stock solution of each MIP is added. In this way, in the presence of the DNA polymerase activity and appropriate dNTPs and in the presence of ligase activity, a large number of ligated products will be produced that reflects the number of repeats present in the genome. The use of excess MIPs relative to genomic DNA is in contrast to the traditional teaching of classic MIPs assays, where using high levels of MIPs relative to genomic DNA would simply increase the likelihood of generating non-specific and (undesired) linear products and decrease the likelihood of generating (desired) circularized products.

The MIPs and genomic DNA are incubated in the presence of reagents and enzymes allowing the extension of hybridized 3' MIPs, and the subsequent ligation of the extended 3' ends to 5' ends bound to the same template within the same tandem repeat unit. In one embodiment, a first hybridization step is performed, including the following components: genomic DNA, MIPs targeting the tandem sequences of interest (e.g., a MIP targeting the telomere and a MIP targeting the ATGG repeat), an appropriate buffer (e.g., 10x Amp ligase buffer), and water to the desired final volume. The hybridization step can be carried out according to standard methods, e.g., using a thermocycler with the following temperature cycles: 1. 95° C. for 10 minutes; 2. 72° C. for 1 minute, with a slow ramp rate (e.g., 0.1° C./s); 3. 56° C. for 5 minutes, with a slow ramp rate (e.g., 0.1° C./c); 4. Goto step 2 10x; and 5. 56° C. for 16 hours.

Following hybridization, a gap filling and ligation step is performed, in which, e.g., the following reagents are added to the hybridization mixture: ligase (e.g., 5U of Amp ligase; e.g., from Lucigen), DNA polymerase (e.g., 0.6U of T4 polymerase; e.g., from New England Biolabs), appropriate deoxyribonucleoside triphosphates (e.g., dGTP, e.g., 2.5 µl of a 2.5 mM stock solution), BSA (e.g., 1×), and buffer (e.g., Amp ligase buffer) and water to appropriate final buffer concentration and total volume. The gap filling and ligation is then performed according to standard methods, e.g., using a thermocycler with the following temperature cycle: 37° C. for 30 minutes; 75° C. for 20 minutes.

The above experimental conditions are provided for illustrative purposes, and it will be appreciated that the experimental conditions and/or nature, quantity, or presence or absence of the different reagents used can be varied in all of the present reaction steps, e.g., regarding the temperature, duration, or number of cycles for the hybridization, gap filling/ligation, and amplification steps, and regarding the reagents used. Such optimization of the reaction conditions is well within the abilities of one of ordinary skill in the art. In some embodiments, higher concentrations of the MIPs and/or the dNTPs than those described above are used in the reactions.

As described elsewhere herein, the present methods typically omit an exonuclease step (in contrast to traditional MW-based assays), although a short exonuclease treatment can be included to remove unligated MIPs or for quality control or comparison purposes.

5. Generated Products and Control Measures Using a New Experimental Design

As described above, when the hybrization, extension and ligation reactions are performed in the presence of only those deoxynucleotides needed to cover the gap between a 3' and 5' end bound to the same template within a single repeat, there are two types of products that can be generated. The first, generated when the 5' and 3' ends belong to the same MIP, is a circularized, ligated product. Such circularized products correspond to the desired products of previous MW assays. The second product, generated when the 5' and 3' ends belong to different MIPs, is a ligated linear product (or "LL-MIP"). In classical MIP assays, all linear products are removed, e.g., through exonuclease activity, and the only products subject to quanitification, detection, or analysis are the circular products.

Figure 8:
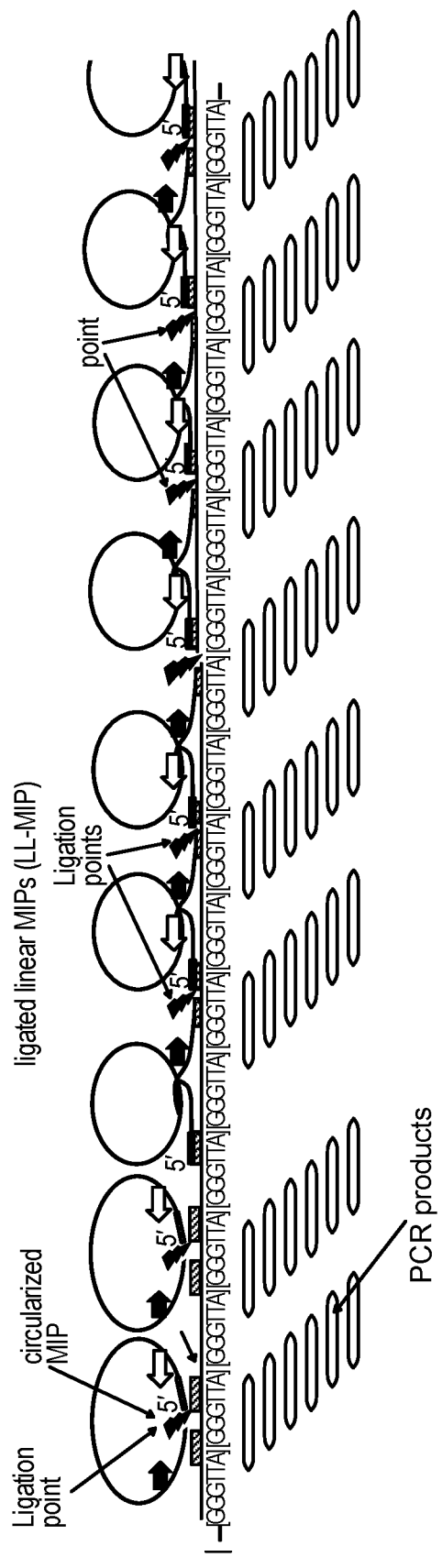
FIG. 8. Schematic workflow to quantify ligation points after hybridization and ligation reactions. Each ligation point represents a unit of length of the targeted tandem repeat. A method, e.g. qPCR, is used to quantify the abundance of ligation points. The normalized abundance can then be used as a biomarker of the length of the tandem repeat. It could also be converted into a unit of length (e.g. kbp in the case of telomeres) by calibrated samples using a regression equation such as that shown in the Examples and in FIG. 5. Figure discloses SEQ ID NO: 39.

The present methods give rise to several types of products, including circularized MIPs described in various classical MIP assays, and the new ligation product called LL-MIPs, which comprise two or more MIPs. In particular, because of the large number of binding sites for the MIPs that are present within long tandem repeats, and because of the high concentrations of MIPs that are used in the present methods relative to the concentration of genomic DNA, multimeric forms are produced in which 3, 4, 5, 6, 7, 8, 9, 10 or more MIPs are ligated together. Together these products reflect the copy number of the tandem repeat in the genome. As a circularized probe reflects one ligation event (ligation point in FIG. 1), similarly a LL-MIP comprising two MIPs also reflects one ligation point, and both represent one length unit of the tandem repeat. Further, LL-MIPs comprising more than two MIPs reflect multiple ligation events and therefore multiple length units of the targeted tandem repeat, e.g., telomere. In general, the number of ligation events for an multimeric LL-MIP comprising n MIPs is n-1. Accordingly, in numerous embodiments of the present invention, all ligated products obtained in the methods, including circular products as well as ligated linear products comprising 2 or more individual MIPs ligated together, are retained and quantified in order to determine the overall size, i.e., copy number, of a tandem repeat sequence such as a telomere. The overal abundance of ligation points or copy number of such motif represents the length of the telomere or other tandem repeat (FIG. 8).

The telomere repeat motif [GGGTTA] is composed of 3 types of nucleotides, namely, G, T, and A. While the binding sites of the 5' and 3' ends of MIPs are randomly distributed, some may bind to the same motif while others may span multiple repeats. For the quantification of telomere length, it is necessary that only those MIP ligations occuring within the same individual motif proceed to the subsequent reaction steps and are counted. This can be achieved by limiting the number of dNTPs used in the gap-filling reaction step to at most two dNTPs. In one embodiment, only one dNTP (dGTP) is used in the gap-filling reaction. It will be appreciated, however, that this requirement is not critical for the other, reference (stable) tandem repeat. For example, when the [AAGG] tandem repeat is used as the reference tandem repeat in the telomere length quantification reaction, both dATP and dGTP can be provided in the gap filling reaction.

6. Isolation, Detection, and/or Quantification of Product

As noted elsewhere herein, in previous MIP-based assays all linear products are removed by either enzymatic approaches (using, e.g., a combination of exonucleases, including exonuclease III) or via affinity binding (using, e.g., biotin labeled MIP with open 5' ends). In the context of measurements of telomere length or of other tandem repeat sequences, this is inappropriate as it would falsely lower the calculated size (i.e., copy number) of the telomere or other repeated sequence. This is because telomere length is proportional to the total number of ligation points, regardless of whether the points are within a circularized product or an LL-MIP.

Accordingly, in one embodiment, no exonuclease is used in the present methods to quantify the size of the telomere or other tandem repeat. In some embodiments, however, only exonuclease I is used, and only at a limited level (e.g., less than 1, 2, 3, 4, 5, 10, 15, or 20 units) and for a limited duration (e.g., for up to 1 hour, or for 5, 10, 15, 20, 25, 30, 35, 40, 45, 50, or 55 minutes), in order to remove free (i.e., non-ligated) MIP probes but without degrading ligated linear MIPs.

The abundance of ligation points in ligated products obtained using the present methods, including both circularized and linear products (LL-MIPs), can be quantified in any of a number of ways, including by relative quantification by qPCR, with or without reference samples and/or efficiency correction; by absolute quantification by qPCR, e.g., using precisely measured amounts of cloned MIP products as calibrator samples; by digital PCR, e.g., by droplet digital PCR; or by sequencing, e.g., high throughput sequencing to count the number of various MIP products.

In one embodiment, the abundance of ligation points in circularized and ligated linear MIPs is quantified using PCR, e.g., qPCR using TaqMan probes or other standard methods. For example, qPCR can be performed using a primer common to all of the MIPs used in the reaction (e.g., a common forward primer), together with MIP-specific primers (e.g., a reverse primer specific to each MIP). In one embodiment, the common forward primer is longGC_M13_F (ggcgcatggcTCA CAC AGG AAA CAG CTA TGA C (SEQ ID NO: 16)). When performed for determining telomere length, in one embodiment the telomere-MIP-specific reverse primer is longGC_Link_R_tel tail (gcgcatgtgaATC GGG AAG CTG AAG TAA CC (SEQ ID NO: 11)), and the ATGG-MIP-specific reverse primer is longGC_Link_ R_ATGG (gcatggcgacaATC GGG AAG CTG AAG CCA tccat (SEQ ID NO: 17)). Further, when performed in a TaqMan assay, probes specific to each MIP can be used, such as Taq-3-Telo (for telomere MIPs; /56-FAM/TA GGG TTA G/ZEN/G GTT AGG GTT/3IABkFQ (SEQ ID NO: 18)) and Taq-3-ATGG (for ATGG MIPs; /5HEX/GG ATG GAT G/ZEN/G ATG GAT GGA T/3IABkFQ (SEQ ID NO: 19)).

Such reactions can be performed according to standard methods, e.g., with the following reagents: MIP product (e.g., 5 μl); PCR master mix (e.g., 7.5 μl of a 2× stock solution); Common forward primer (e.g., Primer M13_F; 0.375 μl of a 20 μM stock solution); Reverse primer for MIP 1 (e.g., telomere reverse primer; 0.375 μl of a 20 μM stock solution); Reverse primer for MIP 2 (e.g., ATGG reverse primer; 0.375 μl of a 20 μM stock solution); TaqMan probe for MIP 1 (e.g., Taqman-telo; 0.3 μl of a 10 μM stock solution); TaqMan probe for MIP 2 (e.g., Taqman-4bp; 0.3 μl of a 10 μM stock solution); and water to a final volume of 15 μl.

The quantitative PCR can be performed on a thermocycler, e.g., a Roche LC480 thermocycler using standard temperature cycles, e.g., 1. 95° C. for 10 minutes; 2. 95° C. for 10 seconds; 3. 65° C. for 30 seconds; 4. 72° C. for 10 seconds; 5. Goto step 2 40×.

It will be appreciated, however, that the amounts of each reagent, e.g., each primer, and other reaction conditions, e.g., the temperature cycles used, can be varied in order to obtain optimal results; such optimization of reaction conditions is well within the ability of one of ordinary skill in the art.

In some embodiments, the MIP products are assessed using next generation sequencing (NGS), which is capable of determining nucleic acid sequences, e.g., of probes or probe products, in a massively parallel fashion. Exemplary NGS technologies include, e.g., sequencing by synthesis (Illumina, Inc., San Diego, Calif.), single-molecule real-time sequencing with zero-mode waveguides (Pacific Biosciences of California, Inc., Menlo Park, Calif.), pyrosequencing, ion semiconductor sequencing (Thermo Fisher Scientific Corporation, Carlsbad, Calif.), and sequencing by ligation (Thermo Fisher Scientific Corporation, Carlsbad, Calif.). Typically for genomic sequencing by NGS technologies, full length nucleic acid (e.g., gDNA) is broken into "template" fragments. The templates are then commonly captured or immobilized at spatially separated detector positions allowing hundreds to billions of sequencing reactions to be performed simultaneously. In some cases, the templates must be amplified before sequencing to allow sufficient signal.

7. Determining Tandem Repeat Sequence Copy Number

Once the ligated MIP products have been quantified using, e.g., qPCR, the length of the variable tandem repeat sequence region of the genome is determined. This determination can be done in any of a number of ways, e.g., calculated from a parameter based on the relationsip between the abundances of the target (e.g. telomere) and stable control tandem repeats as obtained by qPCR, digital PCR, or high throughput sequencing of the ligated MIP products. Such methods are outlined and illustrated in the Examples below.

In one embodiment, the determination is performed by calculating the delta-delta-Ct of the two qPCRs (i.e., the qPCR for the target MIP and the qPCR for the control MIP), and using a reference sample. For example, the delta-delta- Cts are calculated by determining the Ct for each qPCR, determining the delta-Ct for each sample, i.e., the difference between the Ct for the variable tandem repeat sequence and the Ct for the stable control repeat sequence in the sample, and, after averaging the different delta-Cts for a given sample (if, e.g., the qPCR is performed in duplicate, triplicate, etc.), determining the delta-delta Ct for each sample by determining the difference between the delta-Ct for the sample and that of the reference sample. The reference sample can be any suitable sample in which the size of the variable tandem repeat sequence region is known and/or is appropriate depending on the purpose of the assay in question; for example, for methods of determining telomere length in a patient having or suspected of having cancer, the reference sample can be from a healthy individual free of cancer. Once the delta-delta-Ct has been determined for each sample, it is possible to determine the overall length of the tandem repeat sequence in each sample. For example, assuming an efficiency value of 2, the ratio of the number of ligation points within the variable tandem repeat sequence (e.g., the telomere) to the number number of points within the control tandem repeat sequence (e.g., the ATGG-containing tandem repeat), as 2^(delta-delta Ct). Both the delta-delta-Ct and the ratio values of each sample can be used as a biomarker of tandem repeat, e.g., a new indicator parameter of telomere length.

Various other approaches to quantify the PCR products in qPCR reactions include relative and absolute quantification approaches. In one embodiment, a serial dilution of a reference sample is quantified to obtain Ct values to calculate the overall assay efficiency. Also, a reference sample can be used in all qPCR batches and the samples compared to the same reference sample to remove batch effects due to plate-to-plate variation in qPCR Ct values. These methods, known as the delta-delta-Ct method and the efficiency corrected delta-delta Ct method, can be applied here to quantify the ligation points of both MIPs.

In addition, if a calibrator with a known (given) amount of ligation points is used in the same qPCR with the test samples, absolute quantification of qPCR can be performed. Such an approach is known as absolute quantification of qPCR results. In other embodiments, other methods of quantification of the abundances of ligation points can be performed, including digital PCR and sequencing.

Further, as described in the Examples section below, additional assays can be performed to determine the overall efficiencies of the qPCRs carried out with the different MIPs, as well as the linearity (for, e.g., different starting DNA concentrations) and specificity of the reactions. Further, the products can be amplified by, e.g., conventional PCR, and the products cloned and sequenced, or separated by gel electrophoresis, e.g., to assess the size and nature of the LL-MIP products obtained. Such procedures can be performed, e.g., by kit manufacturers during the kit development stage.

The overall efficiency of an assay can be calculated with a given MIP, incorporating the efficiency of both the MIP hybridization-gap-filling-ligation reaction, and the qPCR reaction, and the calculated overall efficiencies can be used to correct for the difference in slopes of the Ct values for the two (or more) MIPs used in an assay, allowing an indicator value to be obtained corresponding to an efficiency (slope) corrected relative ratio. This value can be used to express the length of the tandem repeat as a ratio as compared to the reference sample. For example, in view of samples with a given telomere length such as in the cancer cell lines shown in FIG. 5, other samples can read out their telomere length values (dependent variable, y-axis) based on the regression line in FIG. 5 using their ratio values as the independent variable (x-axis).

8. Examples

The present invention will be described in greater detail by way of specific examples.

The following examples are offered for illustrative purposes only, and are not intended to limit the invention in any manner. Those of skill in the art will readily recognize a variety of noncritical parameters which can be changed or modified to yield essentially the same results.

Example 1

New MIP-Based Method for Determining the Length of Telomeres or Other Variable Tandem Repeat Sequences In the present example, telomere repeat length is investigated using a telomere motif MIP probe, which comprises the telomere repeat sequence (GGGTTA) at both its 5' and 3' ends, separated by a linker sequence. The length of sequence targeting of the telomere repeat motifs at the both ends of the telomere MIP can range from, e.g., 15 base pairs to 25 base pairs in length.

In order to normalize the amount of input DNA among samples, a second MIP is used to quantify the number of diploid genome equivalents in the sample DNA. In another embodiment, other methods to represent diploid genome equivalents in the sample DNA may also be used. For example, single copy gene can be quantified by qPCR as an indicator for this purpose.

The precise matching/complementarity offered by preferred MIPs of the present invention, e.g., with 100% complementarity between the 5' and 3' homology regions and the target sequence of template DNA, makes it feasible to detect repeat motifs such as telomeres, and common tandem repeat sequences, e.g., the common 4-base pair sequence ATGG, can be used as a normalizing control. ATGG, or another similar 4-bp tandem repeat, is a suitable control repeat for such normalization as it is abundant in the human genome and will be present at roughly similar (stable) levels per diploid genome equivalent among samples taken from different individuals.

The MIP used to quantify this 4-base pair tandem repeat consists of the 4-base pair repeat motif (ATGG in the present example) at both its 5' and 3' ends, separated by linker sequences. As with the telomere-targeting MIP, the length of sequence targeting the ATGG repeat motif at both ends of the 4 base-pair motif MIP, i.e., the 5' and 3' homology regions, can range, e.g., from 15 base pairs to 25 base pairs long.

As both the telomere and 4-base pair repeat motifs are tandem repeats, in which the same 6-base pair or 4-base pair motif is tandemly repeated, this special sequence configuration created new challenges to conventional MIP assay methods, which are all based on the exclusive detection of circularized MIPs after ligation.

Because the 3' and 5' ends of the MIP can hybridize to the identical repeating target motif, with conventional MIP assays there would be no control over how far apart the two ends of the same MIP molecule hybridize. That is, the gap between hybridization locations of the 3' and 5' ends is random and cannot be certain, i.e., it could be within a single repeat motif or it could span multiple repeats.

Figure 2:
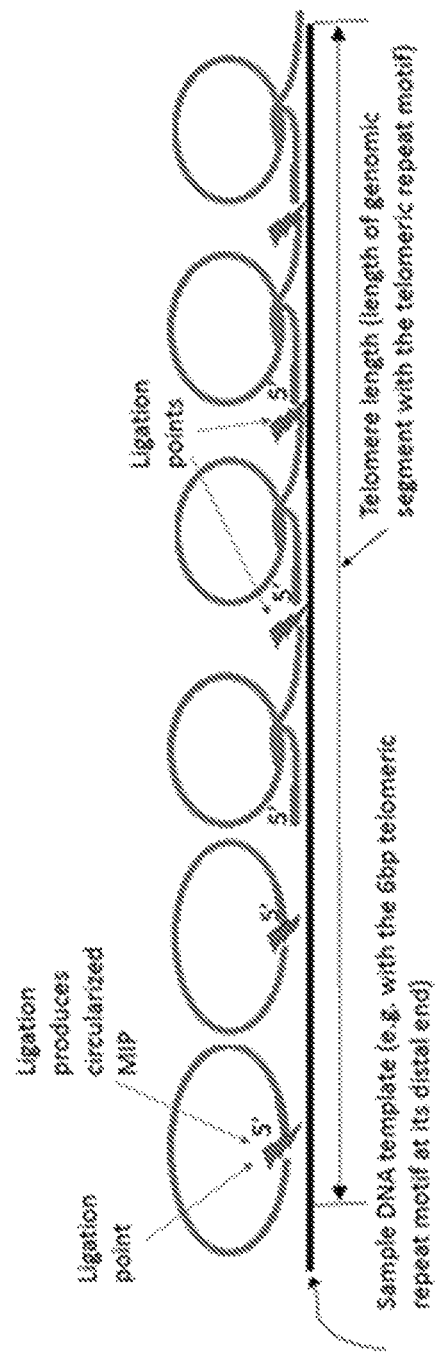
FIG. 2. The principle by which the number of ligation points represents telomere length or number of genomic motif. The abundance of ligation points is an indicator to represent the telomere length.

Accordingly, for the specific purpose of quantifying the length of a telomere or other tandem repeat sequence, if the gap distance between the 3' and 5' ends of the MIP that hybridize to the template DNA is random, the quantification of ligation products as an indicator of telomere length will be problematic, since some ligation products will represent one motif unit while other ligation products will represent 2, 3 or 6 or even more motif units. For example, if the two ends hybridize multiple motifs apart from one another, the quantification will underestimate the abundance of telomere and, accordingly, the telomere length, as the multiple repeat units will be counted as one repeat unit. Therefore, the ideal assay should provide one ligation signal for each motif repeat (FIG. 2). This is achieved in the present methods and compositions in multiple ways, including, inter alfa, by using (1) specifically designed MIP probes, and (2) using limited number of deoxyribonucleotide triphosphates (dNTPs) in the gap-filling/extension step. In one embodiment, the gap between 3' and 5' ends of the telomere MIP is "GG". Similarly, in one embodiment, the gap between 3' and 5' ends of the 4-base pair (ATGG) tandem repeat MIP is "GG".

This design of MIPs, i.e., in which the gap for both the telomere MIP and the 4-base pair repeat MIP is GG, enables the use of dGTP alone in the MIP extension step, with no other dNTPs added. During the extension procedure, only dGTP is present in the reaction mixture, so only MIP molecules with both ends hybridizing next to each other, i.e., with a 2-nucleotide GG gap separating the two ends, will be ligated. In contrast, when the gap between the 5' and 3' ends of the telomere MIP is greater than the 2 nucleotides, i.e., they are separated by more than one repeat motif unit, so the gap comprises "GGGTTAGG", "GGGTTAGGGTTAGG (SEQ ID NO: 36)", or (GGGTTA)nGG and so on, where 'n' is any integer, the ends cannot complete extension and cannot be ligated.

Similarly, when the gap between 3' and 5' ends of the 4-base pair (ATGG) tandem repeat MIP is greater than 2 nucleotides, i.e. they are separated by more than one motif (repeat) unit, so the gap comprises "GGATGG", "GGATGGATGG (SEQ ID NO: 37)" or (GGAT)nGG and so on, where 'n' is any integer, any MIPs with ends hybridizing multiple units apart cannot complete extension and cannot be ligated.

In one embodiment, another telomere MIP is used (called MIP-TelF), of which the gap between 3' and 5' ends is "AGG". In this case, the MIP extension reaction includes only 2 deoxyribonucleoside triphosphates, namely dATP and dGTP, in order to restrict the formation of ligated products to those MIPs whose 3' and 5' ends hybridize to within a single repeat unit, and prevent extension across multiple repeat units.

Sequence of MIP-TelF:

(SEQ ID NO: 1)
5'/Phos/GTT AGG GTT AGG GTT AGG GTT ACTTCAGCTTCC

CGATCCGACGGTAGTGTTCA CAC AGG AAA CAG CTA TGA CTAG

GGT TAG GGT TAG GGT T.

Figure 3:
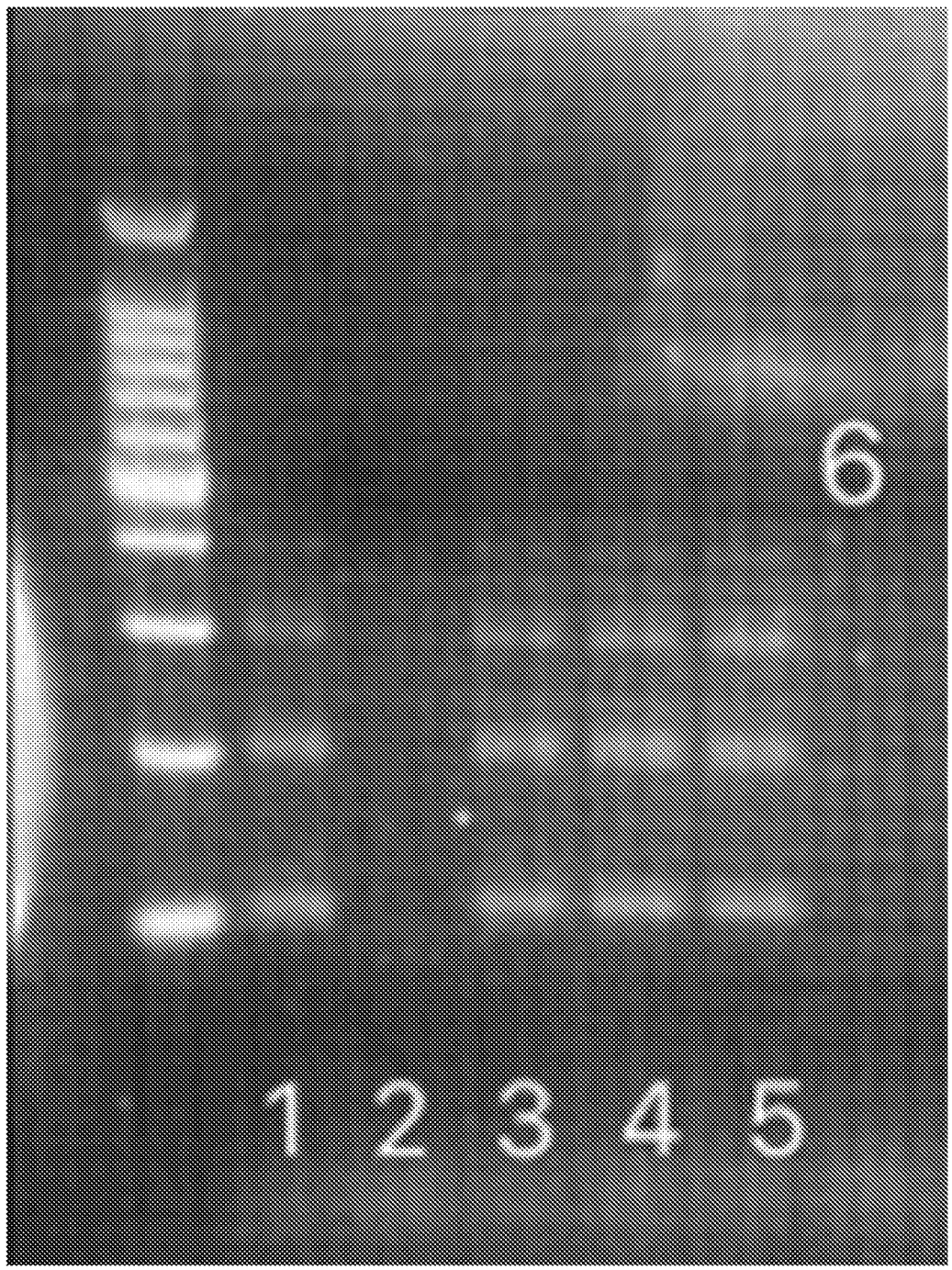
FIG. 3. Gel showing the LL-MIP product after PCR. Lanes 1, 3, 4, 5 show bands of multiples of ~100 bp (the length of a MIP). The size marker on the left shows 100 bp intervals.

The repeating nature of motif units leads to the formation of ligated and linear-MIP products (referred to as LL-MIPs) after ligation (FIGS. 1-3). In previous MIP assays, such linear MIPs would all be removed by either enzymatic methods (e.g., using a combination of exonucleases, including exonuclease III targeting linear double stranded DNA) or methods based on affinity binding (e.g., biotin-labeled MIP with open 5' ends).

However, for the purposes of measuring telomere length, this is inappropriate as it would falsely lower the motif count (i.e., the calculated copy number) of telomeres or other tandem repeat sequences. In fact, we found that a substantial proportion of telomere MIPs formed LL-MIPs after binding to telomere motifs of the sample template (FIGS. 1-3). These LL-MIP were cloned and sequenced to confirm that the sequences contained multiple MIPs and that their targeting sequence was ligated together (FIG. 1C).

In preferred embodiments of the present methods, both circularized MIPs (the traditional MIP product) and LL-MIPs (the new form of MIP product that is specifically retained here, including LL-MIPs comprising 2, 3, 4, 5, 6, 7, 8, 9, 10 or more individual MIPs ligated together) are quantified at the same time. Thus, each ligation point or signal represents a specific unit of telomere length (i.e., one repeat unit within the tandem repeat).

Quantification can be performed by various approaches including but not limited to:
1. Relative quantification by qPCR with or without reference sample and/or efficiency correction.
2. Absolute quantification by qPCR using exactly measured amounts of cloned MIP products as calibrator samples.
3. Digital PCR for example by droplet digital PCR
4. Sequencing, for example, high throughput sequencing to count the number of various MW products.

Example 2

Hybridization, Extension, and Ligation Reactions

Restriction Enzyme Pre-Treatment of DNA Samples

To 50 ng DNA sample, up to 10 units of restriction enzyme, e.g., AluI (New England Biolab) was added and the sample was incubated at 37° C. for 1 hour. The enzyme was then inactivated at 80° C. for 20 min. After centrifugation at 7,000 rpm for 10 min and collection of supernatant, the post-digestion sample can be kept at 4° C.

MIP Hybridization Step

One MIP probe targeting human telomere repeats was used, with a gap of GG, as well as a second MIP targeting the ATGG repeat motif, also with a gap of GG. 5' phosphorylation is needed for all MIP probes.

Probe targeting Telomere repeat motifs (with a gap of "GG"):

MIP-TelF+A:

(SEQ ID NO: 2)
/5Phos/GT TAG GGT TAG GGT TAG GGT TAC TTC AGC TTC

CCG ATC CGA CGG TAG TGT TCA CAC AGG AAA CAG CTA TGA

CTA GGG TTA GGG TTA GGG TTA

Probe targeting 4bp (ATGG) repeat motif (with a gap of "GG"):

MIP-ATGG:

(SEQ ID NO: 20)
/5Phos/AT GGA TGG ATG GAT GGA TGG ATG GCT TCA GCT

TCC CGA TCC GAC GGT AGT GTT CAC ACA GGA AAC AGC TAT

GAC GGA TGG ATG GAT GGA TGG AT

Both probes were designed to leave a gap of "GG" between the 3' and 5' ends when bound adjacently on the template DNA; this two nucleotide gap must be filled in by DNA polymerase before template-dependent ligation can occur.

The hybridization procedures were performed overnight, as follows: (values in brackets are stock concentrations):

| | |
|---|---|
| DNA sample after digestion pre-treatment (10 ng/µl) | 5 µl |
| Amp ligase buffer (10x) | 2.5 µl |
| MIP probe targeting telomer repeat motif (10 nM) | 2 µl |
| MIP probe targeting 4bp repeat motif (10 nM) | 2 µl |
| Water | 15.5 µl |
| Total volume | 25 µl |

The hybridization protocol was performed in a thermocycler, but could equally be performed using other suitable equipment well known in the art, with the following temperature cycles:

| | |
|---|---|
| 1. 95° C. | 10 minutes |
| 2. 72° C. | 1 minute, slow ramp rate, e.g. 0.1° C./s |
| 3. 56° C. | 5 minutes, slow ramp rate, e.g. 0.1° C./s |
| 4. Goto step 2 | 10 times |
| 5. 56° C. | 16 hours |

After the hybridization procedure, the following reagents were added to the 25 µl giving a total of 30 µl (values in brackets are stock concentrations):

| | |
|---|---|
| Amp ligase (5U/µl) | 1 µl |
| T4 polymerase (3U/µl) | 0.2 µl |
| dGTP (2.5 mM) | 2.5 µl |
| BSA (100X) | 0.3 µl |
| Amp ligase buffer (10X) | 0.5 µl |
| Water | 0.5 µl |
| Total additional volume | 5 µl |

Gap filling and ligation temperature protocol was carried out as follows:
37° C. for 30 minutes, then
75° C. for 20 minutes In the present example, no exonuclease treatment was performed, but it could be added here as an optional step. As highlighted elsewhere in the present disclosure, this method is specially designed to detect both circularized MIP (which is also referred as the typical or conventional MIP product) and the new LL-MIP products. Therefore, exonuclease treatment is not needed.

However, for quality control or comparison purposes, e.g., as performed by a kit manufacturer, an exonuclease digestion step can be added. It was also performed in some examples to show that using exonuclease adversely affects the assay performance. In some embodiments, a limited amount of exonuclease 1 can be added (e.g., 20 U for 50 ng of genomic DNA) for a limited amount of time, e.g., up to 1 hour, to remove non-ligated probes but without eliminating ligated linear products.

Example 3

Quantification of Circularized MIP and LL-MIP Products

The total number (or abundance) of ligation points in both circularized MIP and LL-MIP products was quantified to calculate a new indicator of telomere length. Quantification can be performed in any of a number of ways, including, e.g., by (1) quantitative PCR (qPCR) using either relative quantification or absolute quantification approaches, (2) digital PCR, (3) sequencing or (4) any other suitable quantification method.

In typical embodiments, 3 or 4 primers are used to amplify and quantify the abundance of ligation points of the telomere MIP and genome reference MIP (e.g. 4-bp MIP-ATGG). In this example, 3 primers were used in total, as the forward primer (called longGC_M13_F) was common to both the telomere MIP and the genome reference (control) 4bp-MIP-ATGG, and two additional primers were used that were specific to either the telomere-specific probe or the control ATGG probe. A 5' GC rich tail was added to all three primers.

Common and MIP-specific primers used:

```
longGC_M13_F:
                                  (SEQ ID NO: 16)
ggcgcatggcTCA CAC AGG AAA CAG CTA TGA C longGC_Link_R_tel tail:
                                  (SEQ ID NO: 11)
gcgcatgtgaATC GGG AAG CTG AAG TAA CC longGC_Link_R_ATGG:
                                  (SEQ ID NO: 38)
gcatggcgcaATC GGG AAG CTG AAG CCA tccat
```

In this embodiment, two TaqMan probes were used in qPCR to differentiate between the ligation products formed from the two types of MIP probes.

```
Taq-3-Telo:
                                  (SEQ ID NO: 18)
/56-FAM/TA GGG TTA G/ZEN/G GTT AGG GTT /3IABkFQ/

Taq-3-ATGG:
                                  (SEQ ID NO: 19)
/5HEX/GG ATG GAT G/ZEN/G ATG GAT GGA T/3IABkFQ/
```

PCR reaction tube preparation (total volume of 15 µl) was as follows:

| | |
|---|---|
| MIP product (after ligation) | 5 µl |
| PCR master mix (2X) | 7.5 µl |
| Primer M13_F (20 µM) | 0.375 µl |
| Primer tel (20 µM) | 0.375 µl |
| Primer 4bp (20 µM) | 0.375 µl |
| TaqMan-telo (10 µM) | 0.3 µl |
| TaqMan-4bp (10 µM) | 0.3 µl |
| H$_2$O | 0.775 µl |
| Total volume | 15 µl | qPCR was performed in Roche LC480 thermocycler with PCR temperature cycle protocol as follows:

| | |
|---|---|
| 1. 95° C. | 10 minutes |
| 2. 95° C. | 10 seconds |

-continued

| | |
|---|---|
| 3. 65° C. | 30 seconds |
| 4. 72° C. | 10 seconds |
| 5. Goto 2, | 40 cycles |

Variation and Extension of the Typical Experimental Steps

Depending on the property of the sample template or targeting motif, variations of the typical experimental steps presented in the steps above may be implemented, to enhance assay precision and specificity.

Such variations include but are not limited to:

1. Further increases in MIP levels, such as 1.5×, 2×, 4× etc of the given concentration mentioned above.

2. Further increases in the concentration of dGTP or supplied specific nucleoside triphosphate, such as 2×, 4× etc of the concentration mentioned above.

3. Instead of using the second MIP to interrogate a control tandem repeat as an indicator of the diploid genome equivalents present in the sample, other methods can be used in other embodiments. For example, qPCR for a single copy gene or other genetic markers can be performed directly with the input samples to normalize the telomere MIP results.

Example 4

Results

The present indicator of telomere length is derived from the number (abundance) of ligation points formed by the telomere MIP and the number (abundance) of ligation points formed by the genome reference MIP, i.e., the 4-bp (ATGG) MIP used in this example. In this example, the delta-delta-Ct of the 2 qPCRs was used. Ct values of a qPCR from a sample from an adult male were used as reference samples (last three samples in the table). Three cancer cell lines were studied, namely MCF-7, HepG2, and K562. The control sample in the Roche Telomere length measurement kit (Cat. No. 1220913600, Roche Diagnostics GmbH, Germany) and a female sample were also included. All reactions were performed in triplicate, as three different samples and one reaction failed for the K562 cell line. Delta CTs (difference between FAM, Telomeric repeat and HEX, 4bp repeat Ct values) were calculated and average values were obtained for each sample. Then, the delta Ct of each sample was subtracted from that of the Reference sample, obtained from a Male subject, to calculate the delta-delta Ct value. Assuming an efficiency value of 2, the ratio of telomere motif ligation points to genomic 4 base pair (ATGG) motif ligation points could be calculated by 2^(delta-delta Ct). Either delta-delta Ct or the ratio values of each sample (column 7 in Table I, below) could be used as a new indicator of telomere length.

Figure 5:
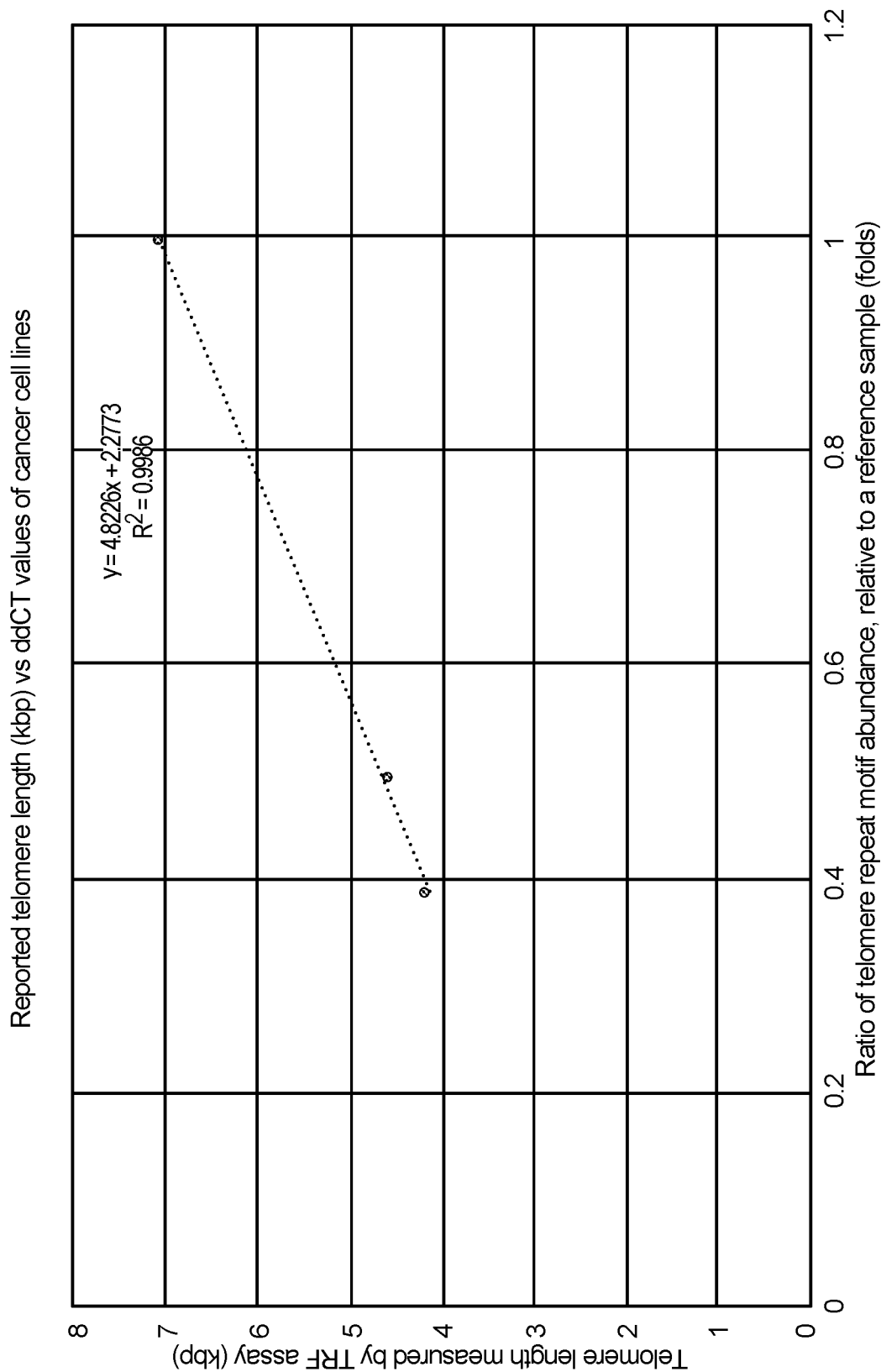
FIG. 5. Correlation between reported telomere length (kbp) measured by TRF assay and the ratio of abundance of ligation points representing telomere motif relative to a reference sample, which were determined from delta-delta Ct values.

The telomere length of several cancer cell lines had been reported in the literature, as measured by terminal restriction fragments (TRF) assays. FIG. 5 shows a high correlation between TRF and the ratio of relative quantification. The regression line in FIG. 5 is used to read out telomere length (y-axis) from any given ratio values (x-axis). The ratio value of the female sample was 1.39, and the estimated telomere length would be 8.98 kbp, according to the regression line shown in FIG. 5.

TABLE I

| Samples | Ct of Telomeric motif | Ct of 4 bp motif | delta Ct | Average delta Ct | delta-delta Ct | ratio as a new indicator of telomere length (fold difference to the reference male sample) | Reported Telomere length (kbp) in literature |
|---|---|---|---|---|---|---|---|
| MCF7 | 20.73 | 21.21 | 0.48 | 0.54 | −1.37 | 0.39 | 4.2 |
| MCF7 | 20.61 | 21.17 | 0.56 | | | | |
| MCF7 | 20.46 | 21.05 | 0.59 | | | | |
| K562 | 19.82 | 20.7 | 0.88 | 0.90 | −1.02 | 0.49 | 4.6 |
| K562 | N.A. | N.A. | N.A. | | | | |
| K562 | 19.6 | 20.51 | 0.91 | | | | |
| HepG2 | 19.27 | 21.21 | 1.94 | 1.91 | 0.00 | 1.00 | 7.1 |
| HepG2 | 19.61 | 21.31 | 1.7 | | | | |
| HepG2 | 19.09 | 21.17 | 2.08 | | | | |
| Female | 17.33 | 19.8 | 2.47 | 2.38 | 0.47 | 1.39 | |
| Female | 17.64 | 19.95 | 2.31 | | | | |
| Female | 17.48 | 19.85 | 2.37 | | | | |
| Kit control sample | 18.88 | 20.43 | 1.55 | 1.56 | −0.35 | 0.79 | |
| Kit control sample | 18.86 | 20.44 | 1.58 | | | | |
| Kit control sample | 18.88 | 20.44 | 1.56 | | | | |
| (Reference sample) | | | | | | | |
| Male | 17.9 | 19.84 | 1.94 | 1.91 | 0.00 | — | |
| Male | 17.91 | 19.88 | 1.97 | | | | |
| Male | 18.05 | 19.87 | 1.82 | | | | |

Example 5

Demonstration of Linearity Response of the Invention

The same reference sample from the male sample in examples 2-4 was diluted into a series of different DNA concentrations so that different amounts (abundance) of telomere repeats were present in the samples. They were prepared into samples with these total DNA amounts: 50 ng, 37.5 ng, 25 ng, 12.5 ng and 6.25 ng. Triplicates of each of these 5 concentrations were used for the telomere assay of this invention. That is, a total of 15 separate reactions were performed. The results are shown in Table II below.

Figure 6:
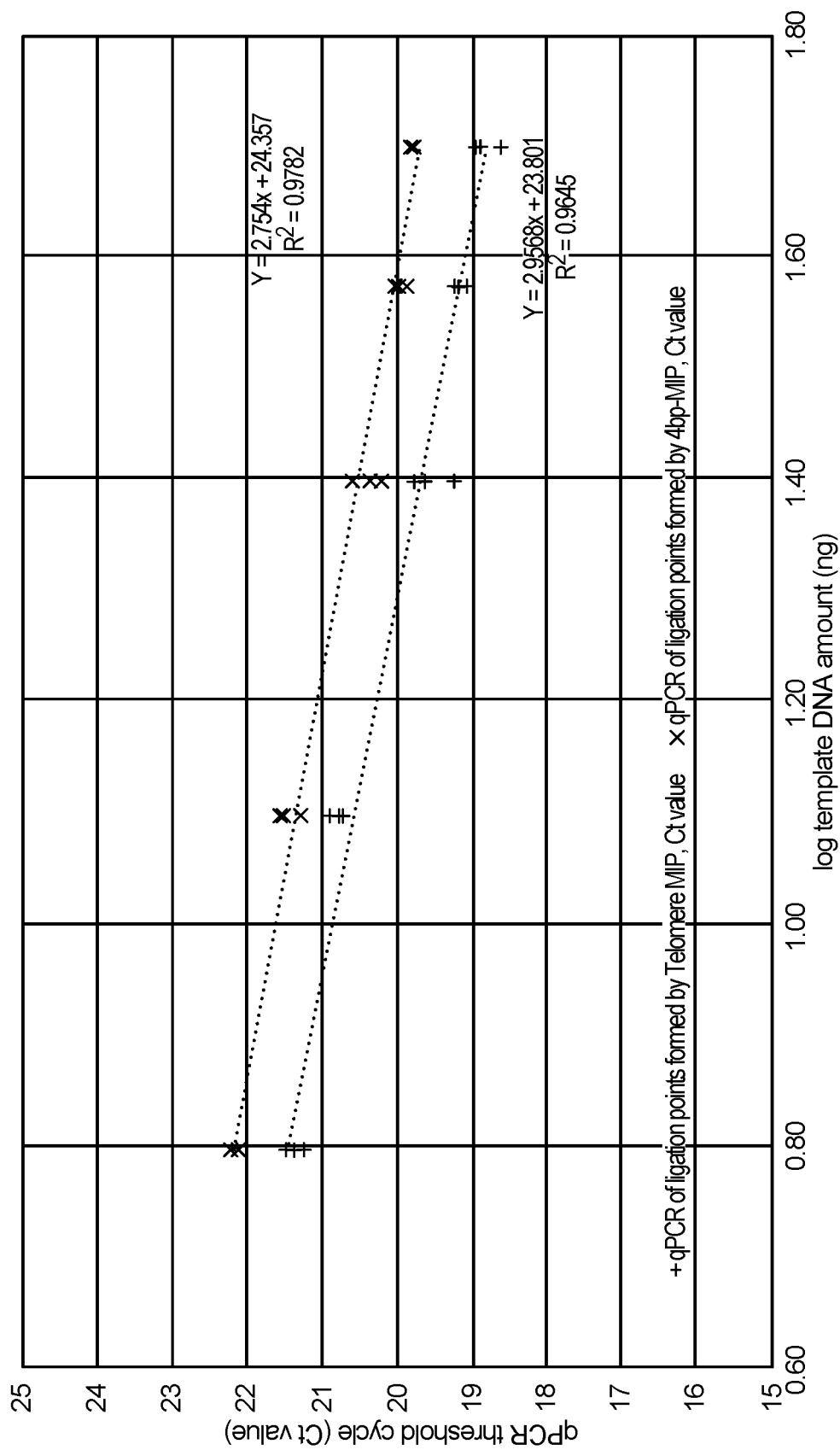
FIG. 6. Example and data showing that the present method had a proportional response (linearity) to the amount of DNA template added.

Input DNA amount was log transformed and the results are shown on the X axis of FIG. 6. The threshold cycles (Ct values, also known as Cq in other reference texts) of qPCR of the 2 MIP targets were plotted against input DNA input amount in this relative quantification analysis.

Quantification of the abundance of both targets (ligation points of telomere and ATGG MIPs) by qPCR showed a good linearity between the input DNA amount and the respective threshold cycles. The coefficients of determination (r2) were 0.96 and 0.98.

The slopes of the 2 regression lines were −2.96 and −2.75, respectively. An overall efficiency of the assay can be calculated in a way similar to calculation of qPCR efficiency using serial dilution samples. However, this overall combined efficiency of the MIP assay incorporates the efficiencies of 2 separate reactions, namely the MIP hybridization-gap filling-ligation reaction and the qPCR quantification reaction.

The overall efficiency is calculated as $10^{(-1/\text{slope})}$. Therefore, the efficiency of the MIP assay for telomere length and for the 4-base pair (ATGG) repeat motif were 2.2 and 2.3, respectively.

TABLE II

Results of various input DNA amount by serial dilution of one sample.

| Input amount of DNA template (ng) | log amount | qPCR of ligation points formed by Telomere MIP, Threshold cycle (Ct value) | qPCR of ligation points formed by 4bp-MIP, Threshold cycle (Ct value) |
| --- | --- | --- | --- |
| 50 | 1.70 | 18.88 | 19.75 |
| 50 | 1.70 | 18.93 | 19.78 |
| 50 | 1.70 | 18.59 | 19.82 |
| 37.5 | 1.57 | 19.04 | 19.86 |
| 37.5 | 1.57 | 19.17 | 19.98 |
| 37.5 | 1.57 | 19.22 | 20.01 |
| 25 | 1.40 | 19.61 | 20.36 |
| 25 | 1.40 | 19.21 | 20.21 |
| 25 | 1.40 | 19.77 | 20.59 |
| 12.5 | 1.10 | 20.7 | 21.28 |
| 12.5 | 1.10 | 20.87 | 21.55 |
| 12.5 | 1.10 | 20.75 | 21.52 |
| 6.25 | 0.80 | 21.36 | 22.1 |
| 6.25 | 0.80 | 21.46 | 22.21 |
| 6.25 | 0.80 | 21.23 | 22.11 |

Example 6

Demonstration of Specificity of the Assays Against the Targeted Motif

Both water blank control sample and DNA of Caenorhabditis elegans (C. elegans, commonly known as roundworm), whose telomere repeat motif is different from humans, were used to show the invention can discriminate between target motifs from non-specific DNA (C. elegans) or a water blank.

TABLE III

| Negative control sample type | qPCR of ligation points formed by Telomere MIP, Threshold cycle (Ct value) | qPCR of ligation points formed by 4bp-MIP, Threshold cycle (Ct value) |
| --- | --- | --- |
| Water blank | 24.32 | 24.97 |
| Water blank | 25.29 | 25.62 |
| Water blank | 24.97 | 25.47 |

Three C. elegans DNA samples (50 ng each) were used in the assay. The standard protocol in examples 2-3 was used.

TABLE IV

| Negative control sample type | qPCR of ligation points formed by Telomere MIP, Threshold cycle (Ct value) | qPCR of ligation points formed by 4bp-MIP, Threshold cycle (Ct value) |
| --- | --- | --- |
| C. elegans DNA, 50 ng | 25.81 | 25.53 |
| C. elegans DNA, 50 ng | 25.85 | 25.58 |
| C. elegans DNA, 50 ng | 25.77 | 25.55 |

The results showed that the abundance of ligation points in the water blank control was only ~1/32 (difference in Ct value of more than 5 cycles, e.g. 24.32−18.88=5.44) of a typical human sample used for this telomere assay (50 ng). Therefore, the method showed a 30x specificity to targeted genomic motifs. C. elegans had results similar to the water blank control.

Example 7

Demonstration of Ligated and Linear MIP (LL-MIP) Products

Six samples were used for the Telomere MIP protocol as in Examples 2-3, except for step 5, in which the TaqMan probe was not added. Instead, a conventional PCR was performed. A higher hybridization temperature (69.3° C.) was used and only one pair of primers (namely longGC_M13_F and longGC_Link_R_tel tail) targeting both types of telomere MIP ligation products was present in this conventional PCR reaction. Then, the PCR products were separated by size on a 4% agarose gel. The smallest size band (~100 bp) represents the typical circularized MIP product with one ligation point. Then, the ~200 bp band represents a LL-MIP with 2 MIPs ligated together, and so on.

Gel results are shown in FIG. 3. 100 bp interval size markers are shown on the left. The effects of omitting the exonuclease digestion step and various amounts of Exonuclease I (New England Biolab) are shown. The results show that the Exonuclease digestion step can be omitted. Similar results were also obtained when only less than 20 units of Exonuclease I was used for not more than 1 hour. If this amount and/or duration was exceeded, degradation of LL-MIP (PCR products longer than ~100 bp) was observed. Addition of other exonuclease (such as Exonuclease III or Exonuclease VII in the conventional MIP assay) caused degradation of the LL-MIP product and detrimentally affected the results of the assay performance of this invention.

TABLE V

| | Samples | Exonuclease used and amount |
|---|---|---|
| Lane 1 | 50 ng human DNA | No Exonuclease digestion step. |
| Lane 2 | No human DNA control | — |
| Lane 3 | 50 ng human DNA | Exonuclease I only digestion: 10 unit for 1 hour |
| Lane 4 | 50 ng human DNA | Exonuclease I only digestion: 20 unit for 1 hour |
| Lane 5 | 50 ng human DNA | Exonuclease I only digestion: 40 unit for 1 hour |
| Lane 6 | No human DNA control | — |

Example 8

Cloning of PCR Product from Example 4 to Confirm the LL-MIP Represented the Target Genomic Motif PCR products obtained from conventional PCR similar to Example 7 were used for cloning and DNA sequencing to confirm that the LL-MIP products were specific to the target genomic motif. TA cloning kits for direct cloning of PCR products (Invitrogen, USA) were used to directly clone the PCR products generated from primers (longGC_M13_F and longGC_Link_R_tel tail).

Positive clones with inserts were selected for sequencing, and those with LL-MIP inserts were longer than the expected insert size of ~100 bp of a conventional circularized MIP product. The insert size of two longer clones were longer than 400 bp. One insert represented a LL-MIP with 6 MIPs ligated together, as schematically shown in FIG. 1B. The target genomic motif was shown as TAACCC, which is the exact complementary sequence of the GGGTTA telomere motif.

The sequencing results of this clone insert are shown in FIG. 1C.

Example 9

Figure 7:
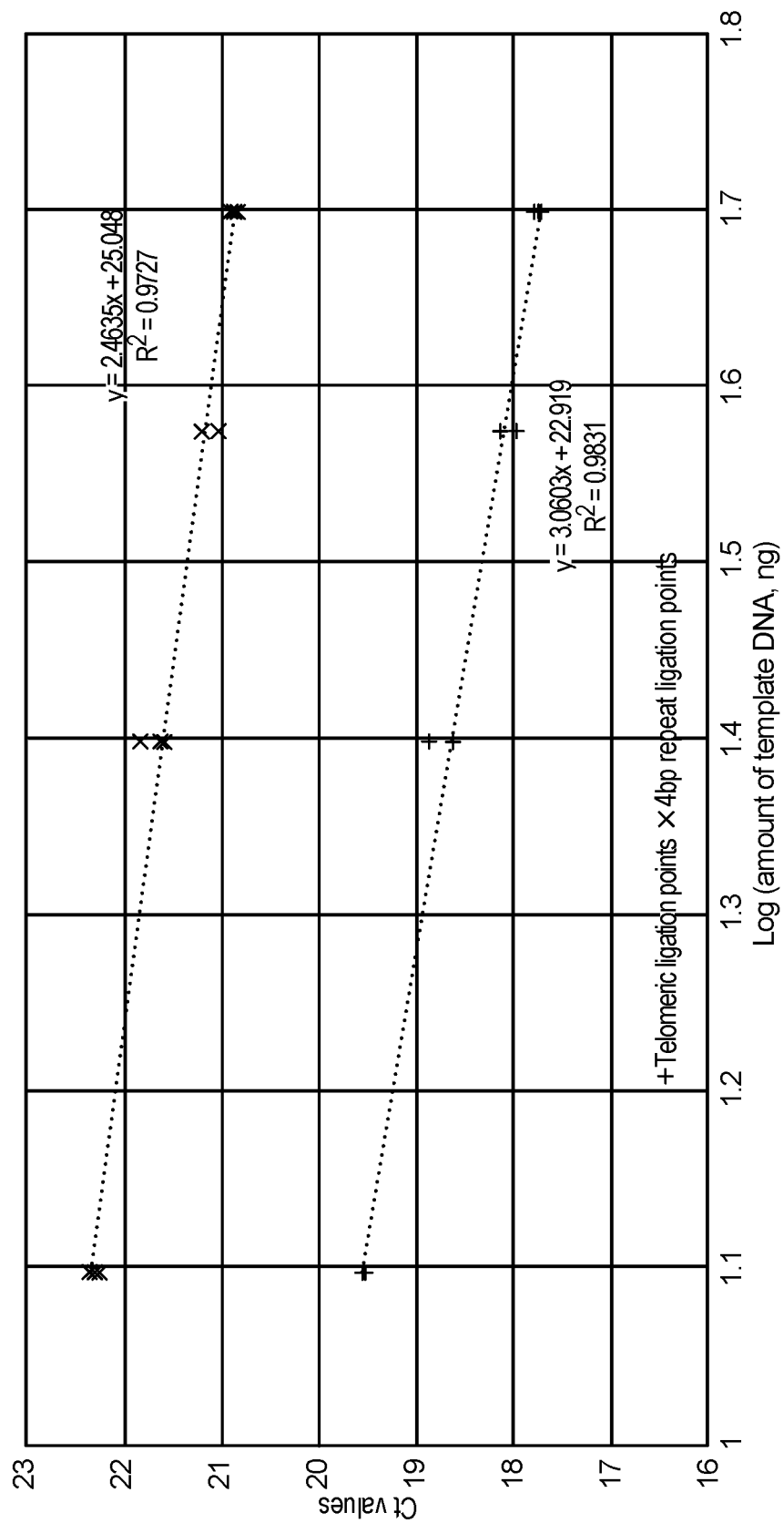
FIG. 7. Example and data that was used in efficiency (slope) corrected delta-delta Ct quantification. This delta-delta Ct value can be used as another measurement of telomere length. In this example, the short MIPs were used in the hybridization reaction.

Alternative MIP Probe Design with Fewer Hybridization Bases (17 bp) to the Target Motif (FIG. 7)

Another set of MIPs targeting the telomere and 4 bp motifs was also designed and successfully tested. The sequences of the 2 MIPs are:

ShortMIPtelo:
(SEQ ID NO: 3)
/5Phos/G GT TAG GGT TAG GGT TAC TTC AGC TTC CCG
ATC CGA CGG TAG TGT TCA CAC AGG AAA CAG CTA TGA C
GG TTA GGG TTA GGG TTA ShortMIP4bp:
(SEQ ID NO: 21)
/5Phos/G ATG GAT GGA TGG ATG GCT TCA GCT TCC CGA
TCC GAC GGT AGT GTT CAC ACA GGA AAC AGC TAT GAC TGG
ATG GAT GGA TGG AT Both MIPs hybridize to the respective target repeats with hybridization ends of 17 basepairs in length. Other conditions were the same as typical experimental steps, except a lower hybridization temperature of 50° C. was used. The reference human DNA sample was used as a template. Different input amounts of template DNA were used as test samples, to examine the linearity and precision of the measurement of ligation points as an indicator of the amount of telomeric motifs present in the sample. Four samples of input DNA of 50 ng, 37.5 ng, 25 ng and 12.5 ng were evaluated. A water blank control was also included. All samples were performed in triplicate to evaluate assay precision.

The discrimination between the typical DNA amount used in the assay (50 ng) and water as template control was markedly enhanced with this pair of short MIPs. The difference in Ct for telomere motif and 4 bp (ATGG) motif were >8.5 cycle and ~6 cycle, respectively. These differences corresponded to a specificity of >60 fold.

TABLE VI

Results of various input DNA amount by serial dilution of one sample using the short MIP design (results are plotted in FIG. 7)

| Amount of Human DNA (ng) | log amount | Ct value of qPCR of Telomeric ligation points | Ct values of qPCR of 4bp repeat ligation points | Another indicator of telomere length: Overall Efficiency corrected relative ratios | Mean value of each triplicates |
|---|---|---|---|---|---|
| 50 | 1.6990 | 17.74 | 20.84 | 0.964 | 0.990 |
| 50 | 1.6990 | 17.71 | 20.87 | 1.014 | |
| 50 | 1.6990 | 17.79 | 20.91 | 0.991 | |
| 37.5 | 1.5740 | 18.14 | 21.21 | 1.008 | Reference |
| 37.5 | 1.5740 | 17.96 | 21.04 | 0.985 | sample |
| 37.5 | 1.5740 | 17.97 | 21.04 | 0.977 | |
| 25 | 1.3979 | 18.63 | 21.61 | 1.013 | 1.038 |
| 25 | 1.3979 | 18.63 | 21.65 | 1.052 | |
| 25 | 1.3979 | 18.87 | 21.84 | 1.049 | |
| 12.5 | 1.0969 | 19.54 | 22.32 | 0.992 | 0.985 |
| 12.5 | 1.0969 | 19.53 | 22.36 | 1.038 | |
| 12.5 | 1.0969 | 19.56 | 22.26 | 0.924 | |
| Water as template | | 26.28 | 26.82 | | |
| Water as template | | 26.27 | 26.84 | | |
| Water as template | | 26.43 | 26.93 | | |

As described in the above examples, an overall efficiency can be calculated for the 2 MW assays. Similar to the relative quantification method in qPCR based on efficiency correction, the overall efficiencies were used in the MIP assay to correct for the difference in slopes of Ct value of 2 motifs. Therefore, an overall efficiency (slope) corrected relative ratio could be analyzed. First, the efficiency (slopes) of two regression lines in FIG. 7 were calculated. The slopes for the telomere motif and the 4 bp (ATGG) motif were −3.06 and −2.46, respectively.

Then, based on the 2 regression lines, the Ct values of a 37.5 ng sample was used as a calibrator sample. Efficiency was calculated as 10^(−1/slope).

The efficiency (Slope) corrected relative ratio of abundance of telomere ligation points to 4 bp (ATGG) motif ligation point relative to the calibrator sample is equal to: [Efficiency of Telomere motif ^ (delta Ct between Reference sample and test sample)]/[Efficiency of 4bp motif ^ (delta Ct between Reference sample and test sample)]

With this indicator value, the efficiency (Slope) corrected relative ratio, the telomere length was expressed as a ratio compared to the reference sample. Mean values of triplicates ranged between 0.985 to 1.038. This is an example of a new indicator of telomere length generated from this novel method. It represented the ratio of telomere length in relation to the reference sample. For example, the 50 ng sample, the telomere length is 0.99x of the reference sample (37.5 ng sample). The expected value is 1 as all samples originated from the same human subject that was also used as the reference sample. The results showed that efficiency (Slope) corrected relative ratio eliminated any bias effect due to differences in the input DNA amount.

Example 10

Other Calculation Methods to Derive Indicator Values of Telomere Length Based on the Abundance of Ligation Points of Telomere MIP and Genome Reference MW Various approaches can be used to quantify the exact amount of PCR products in qPCR including relative and absolute quantification approaches. In another embodiment (see above examples), a serial dilution of a reference sample can be quantified to obtain Ct values to calculate overall assay efficiency. A reference sample can be used in all qPCR batches and samples and compared to the same reference sample to remove batch effects due to plate-to-plate variation in qPCR Ct values. These methods are known as the delta-delta-Ct method and the Efficiency corrected delta-delta Ct method. They are applied here to quantify the ligation points of both MIPs.

In addition, if a calibrator with a known (given) amount of ligation points is used in the same qPCR with test samples, an absolute quantification of qPCR can be performed. Such approach is known as absolute quantification of qPCR results.

In other embodiments, other methods of quantification of the abundances of ligation points can be performed, including digital PCR and sequencing.

Example 11

Further Extension to Quantify Epigenetic Marks

In the DNA sample pre-digestion step, addition of methylation sensitive restriction enzyme to the pre-digestion of DNA sample enables quantification of the extent of methylation at a genomic scale. The results of two reactions from the same sample are compared, namely methylation sensitive restriction enzyme (its ability to cut DNA depends on the presence of methylated nucleotide) and a methylation insensitive restriction enzyme recognizing the same restriction site (isoschizomers). For example, the pair of enzymes, HpaII (methylation sensitive) and MspI, can be used. A new MIP designed to target CpG islands is used together with the genomic reference MIP such as the 4bp (ATGG) MIP used here.

In one embodiment, a specific target genomic region of interest is first isolated by a target-enrichment method, a number of which are known in the art. For example, array-based capture or in-solution capture are useful capture methods that can be used to isolate a target genomic region of interest. After target enrichment, the sample can be processed for quantification of a repeat motif to detect expansion (in length) of the motif. This approach could be used, for example, to detect trinucleotide repeat expansions that are associated with various diseases.

Example 12

Alternative Embodiments

Variations are possible in the experimental steps, MIP targets, probes, primers, and enzyme usage following in the estimation of telomere length. Such variations include:

(a) Shorter duration of hybridization step, for example, 2 hours of hybridization (b) Simpler hybridization temperature protocol (c) Use of other stable short tandem repeats as a target for the second MIP. For example, [AAGG]n tandem repeat can be used as a target. The corresponding MIP to interrogate [AAGG]n is: 5'-GAA GGAA GGAA GGAA GGAA GGGGCGCTTCAGCTTCCC-GATCCGACGGTAGTGTTCA CAC AGG AAA CAG CTA TGA CAA GGAA GGAA GGAA GGAA GG-3' (SEQ ID NO: 22). The phosphorylation and hydroxylation requirements at the ends are the same as in the typical protocol.

(d) Other enzymes having similar properties to those in the typical protocol can be used.

(e) In experiments to scale-up the production phase assay, the duration of the hybridization step can be shortened to 16 hours.

(f) Use of additional probes and primers, as shown in Table VII:

TABLE VII

Additional probes and primers

Additional DNA probes:

MIP probe targeting a 4-bp motif of sequencing of (AAGG)n
AAGG: MIP-2019AAGG pure:
(SEQ ID NO: 9)
/5Phos/ggaaggaaggaaggaaggaaggTCGATCCGACAGCTTCCGTagC GgttTCACACAGGAAACAGCTATGACtcacagaaggaaggaaggaaggaag gaag Additional primers used in qPCR:

Long GC_Telo_F
(SEQ ID NO: 10)
GGTCCGAGCCAGC TAT GAC TAG GGT TAG GG longGC_Link_R_tel tail
(SEQ ID NO: 11)
gcgcatgtgaATC GGG AAG CTG AAG TAA CC

TABLE VII-continued

Additional probes and primers longGC_M13F+6
(SEQ ID NO: 12)
GCTGCCTCGC AGG AAA CAG CTA TGA CTC ACA G longGC_AAGG_R
(SEQ ID NO: 13)
GGTGCGTCGC GCT GTC GGA TCG ACC TTC CTT Taqman Probes:

Taqman_long_Telo (FAM)
(SEQ ID NO: 14)
5'FAM-TA GGG TTA GGG TTA GGG TTA GGGT

Taqman_AAGG (HEX)
(SEQ ID NO: 15)
5'HEX-AAG GAA GGA AGG AAG GAA GG

Example 13

Alternative Embodiment Protocols of Hybridization, Extension, and Ligation Reactions Restriction Enzyme Pre-Treatment of DNA Samples 50-500 ng DNA can be used in individual samples for the quantification of telomere length (TL). To DNA samples, up to 10 units of two restriction enzyme, e.g., AluI and DdeI (New England Biolabs) were added and the samples were incubated at 37° C. for 1 hour. The enzyme was then inactivated at 80° C. for 20 min. After centrifugation at 7,000 rpm for 10 min and collection of supernatant, the post-digestion sample can be kept at 4° C.

MIP Hybridization Step

The same MIP probe targeting human telomere repeats as that in Example 2 was used, with an MIP probe targeting the (AAGG) repeat motif.

Probe targeting Telomere repeat motifs (with a gap of "GG"):

MIP-TelF+A:
(SEQ ID NO: 2)
/5Phos/GT TAG GGT TAG GGT TAG GGT TAC TTC AGC TTC

CCG ATC CGA CGG TAG TGT TCA CAC AGG AAA CAG CTA TGA

CTA GGG TTA GGG TTA GGG TTA

Another probe targeting the (AAGG) repeat motif (with a gap of "GAA"):

MIP-AAGGpure:
(SEQ ID NO: 9)
/5Phos/GG AAGG AAGG AAGG AAGG AAGG TCG ATC CGA CAG

CTT CCG TAG CGG TTT CAC ACA GGA AAC AGC TAT GAC TCA

CAG AAGG AAGG AAGG AAGG AAGG AAG

The hybridization procedures were performed overnight in a hybridization mixture, as follows: (values in brackets are stock concentrations):

| | |
|---|---|
| DNA sample after digestion pre-treatment (10 ng/μl) | up to 15 μl |
| Amp ligase buffer (10x) | 2.5 μl |
| MIP probe, MIP-TelF + A (10 nM) | 3 μl |
| MIP probe, MIP-AAGGpure (10 nM) | 3 μl |
| Water | variable volume |
| Total volume of hybridization mixture | 25 μl |

The hybridization protocol was performed in a thermocycler, but could equally be performed using other suitable equipment known in the art, with the following temperature cycles:

| | |
|---|---|
| 1. 95° C. | 10 minutes |
| 2. 72° C. | 1 minute, slow ramp rate, e.g. 0.1° C./s |
| 3. 50° C. | 5 minutes, slow ramp rate, e.g. 0.1° C./s |
| 4. Goto step 2 | 10 times |
| 5. 50° C. | 16 hours |
| 6. Room temperature | 1 hour |

After the hybridization procedure, 5 μl of hybridization mixture was added to 15 μl of gap filling and ligation reaction reagent (shown below) which was preheated to 50° C.

Gap Filling and Ligation Step

A gap filling and ligation reaction reagent with both dGTP and dATP was prepared at 37° C. or pre-warmed and kept at 37° C. after preparation: (values in brackets are stock concentrations):

| | |
|---|---|
| Amp ligase (5U/μl) | 0.8 μl |
| T4 polymerase (3U/μl) | 0.15 μl |
| dGTP (10 mM) | 0.5 μl |
| dATP (10 mM) | 0.5 μl |
| BSA (100X) | 0.2 μl |
| Amp ligase buffer (10X) | 1.5 μl |
| Total Volume (top up with water) | 15 μl |

5 μl of hybridization mixture was preheated to 50° C. for 30 minutes before the addition of 15 μl of pre-warmed gap filling and ligation reaction reagent.

Then, the gap filling and ligation reaction was carried out to generate MIP products with ligation points of the 2 MIP probes, as follows:

37° C. for 30 minutes, then

45° C. for 5 minutes, then

95° C. for 10 minutes, then

4° C. and hold.

Quantification of Ligation Point Step

The MIP product after gap filling and ligation can be used for the quantification of ligation points as a measure of genomic motif quantity. In this embodiment, qPCR was used, but other technologies could easily be used as well.

Four primers and two TaqMan probes were used in qPCR.

Long GC_Telo_F
(SEQ ID NO: 10)
GGTCCGAGCCAGC TAT GAC TAG GGT TAG GG

LongGC_Link_R_tel tail
(SEQ ID NO: 11)
GCGCATGTGA ATC GGG AAG CTG AAG TAA CC

-continued

LongGC_M13F+6
(SEQ ID NO: 12)
GCTGCCTCGC AGG AAA CAG CTA TGA CTC ACA G

LongGC_AAGG_R
(SEQ ID NO: 13)
GGTGCGTCGC GCT GTC GGA TCG ACC TTC CTT

Taqman_long_Telo
(SEQ ID NO: 14)
/56-FAM/TA GGG TTA GGG TTA GGG TTA GGGT/3IABkFQ/

Taqman_AAGG
(SEQ ID NO: 15)
/5HEX/AAG GAA GGA AGG AAG GAA GG/3IABkFQ/

The products of gap filling and ligation of all samples, standards and calibrators were diluted 100-fold with water before qPCR. Accordingly, all samples, standards and calibrators had the same dilution factor.

qPCR reaction tube preparation (total volume of 15 μl) was as follows:

| | |
|---|---|
| MIP product (after 100-fold dilution) | 5 μl |
| PCR master mix (2X) | 7.5 μl |
| Primer Long GC_Telo_F (20 μM) | 0.375 μl |
| Primer LongGC_Link_R_tel tail (20 μM) | 0.375 μl |
| Primer LongGC_M13F+6 (20 μM) | 0.375 μl |
| Primer LongGC_AAGG_R (20 μM) | 0.375 μl |
| Taqman_long_Telo (10 μM) | 0.3 μl |
| Taqman_AAGG (10 μM) | 0.3 μl |
| Total volume (top up with water) | 15 μl | qPCR was performed in a Roche LC480 thermocycler with a PCR temperature cycle protocol as follows:

| | |
|---|---|
| 1. 95° C. | 10 minutes |
| 2. 95° C. | 10 seconds |
| 3. 55° C. | 30 seconds |
| 4. 72° C. | 10 seconds |
| 5. Goto 2, | 40 cycles |

Example 14

The Demonstration of a Linear Response and the Indicator Value of Telomere Length is not Affected by Different Starting Amounts of DNA Used for Hybridization A reference sample was diluted into a series of different DNA concentrations so that different amounts (abundance) of telomere repeats and AAGG repeats were present in the samples. They were prepared into samples with these total DNA amounts added to the hybridization reaction: 160 ng, 80 ng, 40 ng, and 20 ng. Duplicates of each of these 4 amounts were used in the telomere assay protocol described in Example 13. The results are shown in Table VIII below. The mean indicator value for telomere length using delta-Ct (difference of the two Ct values of the 2 MIP probes) was 0.945, with a coefficient of variation at 6.32%.

Figure 9:
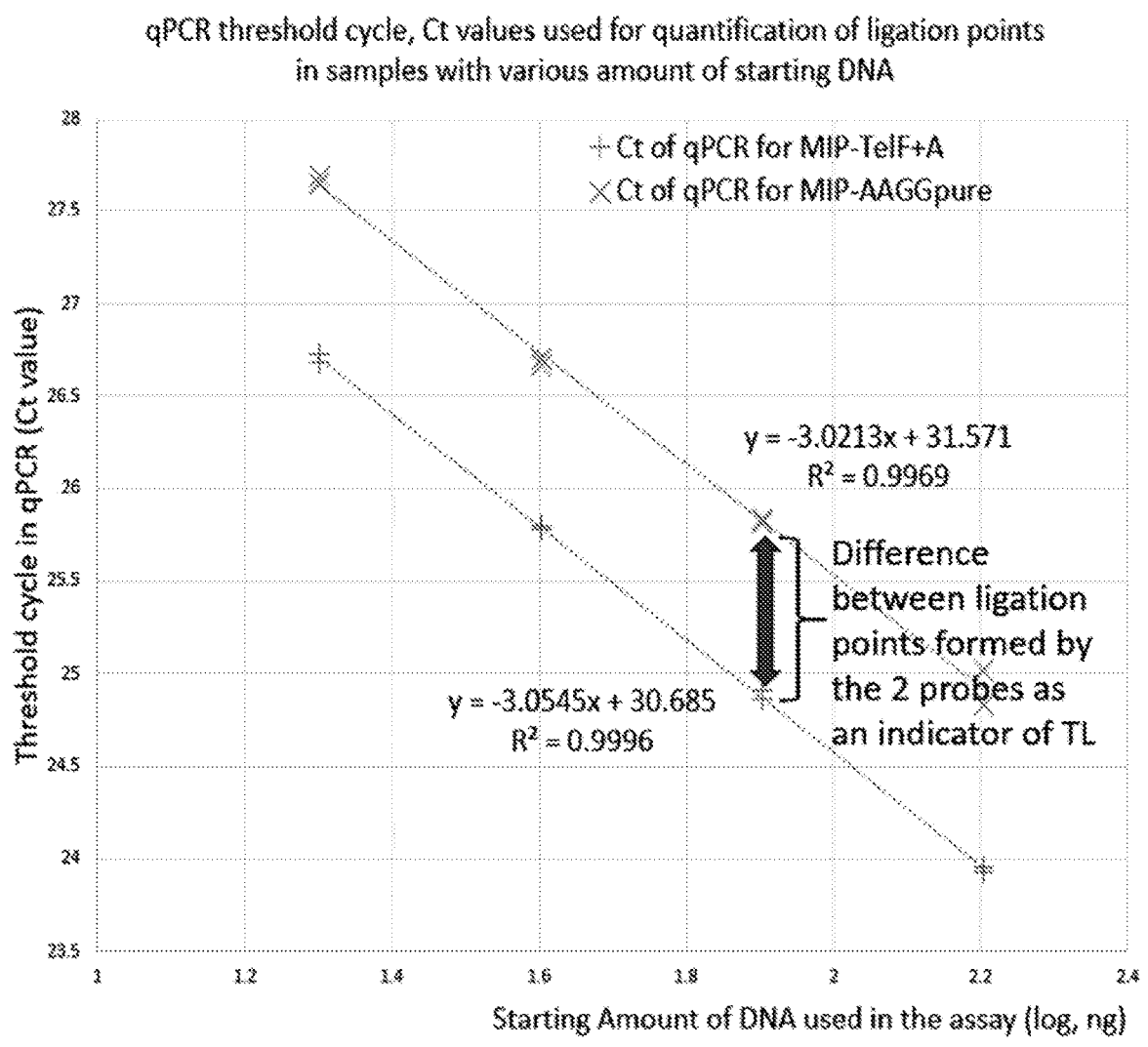
FIG. 9. The indicator value of telomere length is not affected by different starting DNA amounts used for hybridization.

The input DNA amount was log transformed and the results are shown on the X axis of FIG. 9. The threshold cycles (Ct values, also known as Cq in other reference texts) of qPCR of the 2 MIP targets (MIP-Te1F+A and MIP-AAGGpure) were plotted against input DNA amount (log scale) in this relative quantification analysis.

Quantification of the abundance of both targets (representing ligation points formed by MIP-Te1F+A and MIP-AAGGpure, respectively) by qPCR showed a good linearity between the input DNA amount and the respective threshold cycles (Ct values). The coefficients of determination ($r^2$) were 0.999 and 0.997.

The slopes of the two regression lines were −3.05 and −3.021, respectively. An overall efficiency of the assay can be calculated in a way similar to the calculation of the qPCR efficiency using serial dilution samples. However, this overall combined efficiency of the MIP assay incorporates the efficiencies of all the reaction steps involved as described in Example 13, namely the MIP hybridization step, the gap filling-ligation step, and the quantification of ligation points step. In contrast, the efficiency of a qPCR, commonly referred to in a typical qPCR assay, only describes the efficiency of the qPCR.

The overall efficiency is calculated as $10^{(-1/slope)}$ of the results in FIG. 9. Therefore, the efficiency of the MIP assay for MIP-Te1F+A (telomere probe) and MIP-AAGGpure (AAGG probe) were both 2.1. They were close to the ideal efficiency value of 2.

With these near ideal overall efficiency values, telomere length can be easily calibrated by using samples of given or known telomere length values (in kbp). These calibrator samples and samples of unknown TL were assayed together by the method of this invention and then indicator values obtained by quantification of ligation points of calibrator samples and unknown sample can be converted to TL in kbp unit.

As shown in previous examples, the indicator values could be obtained one of these calculation methods: delta-Ct method, delta-delta-Ct method and the Efficiency corrected delta-delta Ct method.

TABLE VIII

Results of the Example 13 protocol with various input DNA amounts.

| Input amount of DNA template (ng) | log amount | qPCR of ligation points formed by MIP-TelF + A (telomere probe), Threshold cycle (Ct value) | qPCR of ligation points formed by MIP-AAGGpure (AAGG probe), Threshold cycle (Ct value) | delta Ct |
|---|---|---|---|---|
| 160 | 2.20 | 23.93 | 24.83 | 0.9 |
| 160 | 2.20 | 23.95 | 25.02 | 1.07 |
| 80 | 1.90 | 24.87 | 25.83 | 0.96 |
| 80 | 1.90 | 24.91 | 25.82 | 0.91 |
| 40 | 1.60 | 25.8 | 26.7 | 0.9 |
| 40 | 1.60 | 25.78 | 26.67 | 0.89 |
| 20 | 1.30 | 26.68 | 27.65 | 0.97 |
| 20 | 1.30 | 26.73 | 27.69 | 0.96 |
| | | | Mean | 0.945 |
| | | | CV % | 6.32% |

With these near ideal overall efficiency values, telomere length can be easily calibrated by using samples of given or known telomere length values (in kbp). These calibrator samples and samples of unknown TL were assayed together by the method of this invention and then indicator values obtained by the quantification of ligation points of calibrator samples and unknown samples can be converted to TL in kbp units.

As shown in previous examples, the indicator values can be obtained by one of the following calculation methods: delta-Ct method, delta-delta-Ct method and the Efficiency corrected delta-delta Ct method.

Example 15

Use of Calibrator Samples to Convert Indicator Values of Ligation Points to TL in Kbp Units The indicator values produced from assay of this invention can be converted to TL in kbp units by using one or more calibrator sample(s) with a given known TL. In an experiment using a procedure similar to that of Example 13, four samples of known TL were assayed. Their indicator values and raw data of qPCR for ligation points of the two probes are shown in Table IX.

The indicator values of TL were based on the efficiency corrected relative ratio of the abundance of telomere (MIP-Te1F+A) ligation points to AAGG motif (MIP-AAGGpure) ligation points as given in Example V. The reference sample in this batch had corresponding Ct values of 23.7 and 24.2, respectively, and the efficiencies of the reactions were 1.88 and 1.85, respectively.

Figure 10:
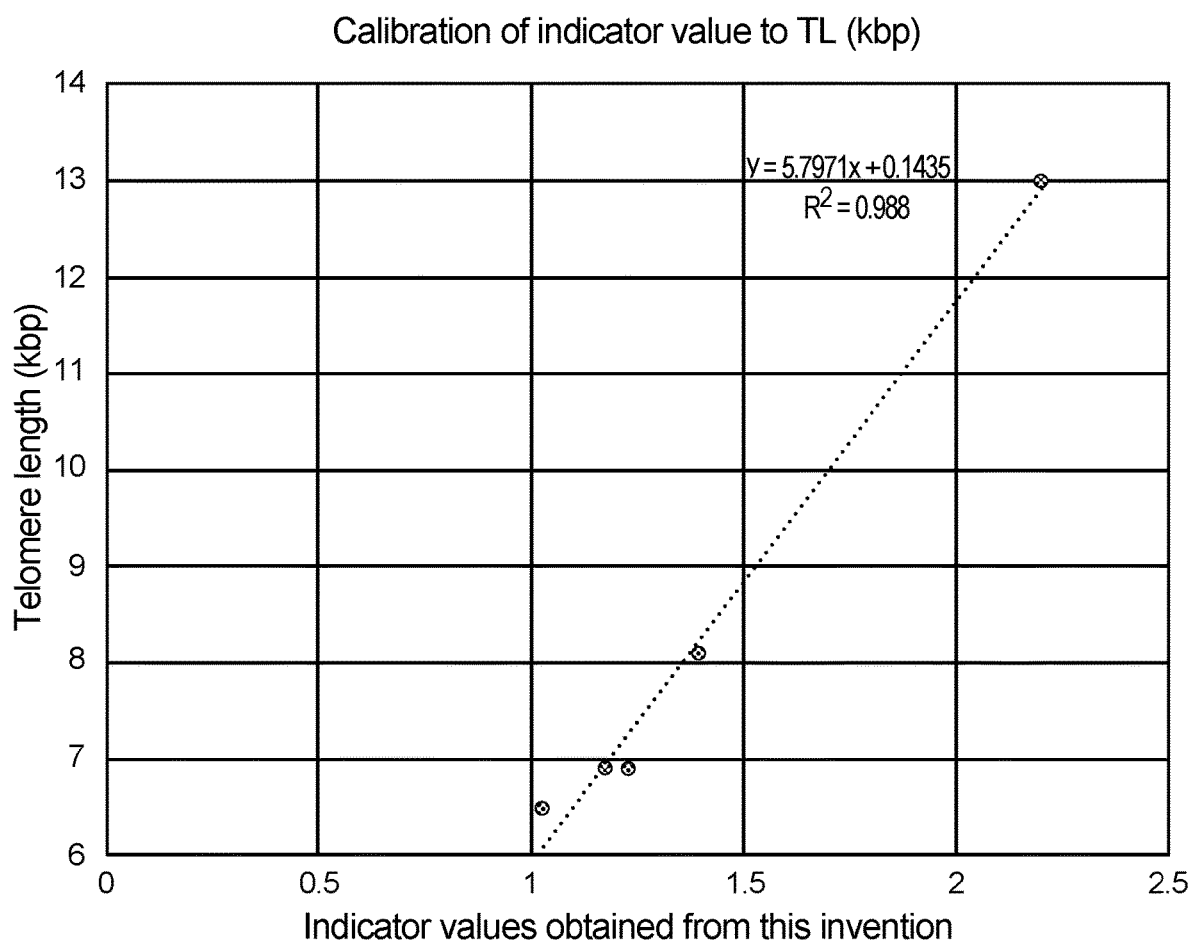
FIG. 10. Calibration of indicator value obtained from this invention method to TL (in kbp unit)

The correlation between TL and the indicator values of these calibration samples is shown in FIG. 10. The correlation of determination (r2) was near 1. The TL of the calibrator samples covers the typical values of TL in human samples.

Based on the regression formula shown in FIG. 10, the TL of other samples of unknown TL can be deduced by the linear regression approach.

TABLE VIII

Results of the quantification of ligation points of calibrator samples.

| Samples | qPCR of ligation points formed by MIP-TelF + A (telomere probe), Threshold cycle (Ct value) | qPCR of ligation points formed by MIP-AAGGpure (AAGG probe), Threshold cycle (Ct value) | Indicator values of ligation points | Known TL (kbp) |
|---|---|---|---|---|
| Subject N | 26.87 | 27.83 | 1.23 | 6.9 |
| Subject N | 27.75 | 28.66 | 1.17 | 6.9 |
| Subject R | 25.85 | 26.98 | 1.39 | 8.1 |
| Cell line Raji | 23.64 | 25.44 | 2.20 | 13 |
| Kit DNA control | 26.6 | 27.25 | 1.02 | 6.5 |

Example 16

Use of Digital Droplet PCR (ddPCR) to Quantify Ligation Points of 2 MIP Probes The ligation points in MIP products formed after gap filling and the ligation step of Example 2, Example 13, or similar embodiments can be quantified by digital droplet PCR to determine an indicator value for the assessment of Telomere length.

This embodiment used MIP products generated by the following MIP probes;

Probe targeting Telomere repeat motifs:

```
MIP-TelF:
                                        (SEQ ID NO: 1)
/5Phos/GT TAG GGT TAG GGT TAG GGT TAC TTC AGC TTC
CCG ATC CGA CGG TAG TGT TCA CAC AGG AAA CAG CTA TGA
CTA GGG TTA GGG TTA GGG TT
```

Probe targeting the alpha satellite sequence of centromere:

```
MIP-Centv2:
                                        (SEQ ID NO: 24)
5'/Phos/gtc TAG GTT TGA TGT GAA GAT Ata ccc gCT TCA
GCT TCC CGA TCC GAC GGT agg ttT CAC ACA GGA AAC AGC
TAT GAC tca cag aaA ACG TTC TGA GAA TGC
```

After the gap filling and ligation step, the MIP product was diluted 50 fold and 5 µl was used in each ddPCR reaction.

Four primers and two TaqMan probes were used in ddPCR.

```
M13_MIP_L2
                                        (SEQ ID NO: 25)
GCGGGCAGGGCGGCtctagaTCACACAGGAAACAGCTATGAC MIP_LinkC-2Ls
                                        (SEQ ID NO: 26)
GGCCCTACCGTCGGATCGGGAAGC M13_Cent_v2-s
                                        (SEQ ID NO: 27)
GGCCTATGACTCACAGAAAACGTTCTGAG Linker_v2-s
                                        (SEQ ID NO: 28)
CTACCGTCGGATCGGGAAG
```

TaqMan probes:

```
Taqman-3-Telo
                                        (SEQ ID NO: 6)
/56-FAM/TAG GGT TAG GGT TAG GGT T/3IABkFQ/

Taq-cent
                                        (SEQ ID NO: 29)
/5HEX/GTC TAG GTT TGA TGT GAA GAT ATA CCC G CTT/
3IABkFQ/
```

Digital PCR (ddPCR) was set up with the following reagents in a total reaction volume of 20 µ1.1: (values in brackets are stock concentrations):

| | |
|---|---|
| ddPCR supermaster (2x) | 10 µl |
| Mg2+ | 0.8 µl |
| Primer MIP_LinkC-2Ls (10 mM) | 0.5 µl |
| Primer M13_MIP_L2 (10 mM) | 0.5 µl |
| Primer M13_Cent_v2-s (10 mM) | 0.5 µl |
| Primer Linker_v2-s (10 mM) | 0.5 µl |
| Taqman-3-Telo (10 mM) | 0.5 µl |
| Taqman-cent (10 mM) | 0.5 µl |

The ddPCR thermocycling protocol was as follows:

| | |
|---|---|
| 95° C. | 5 minutes |
| 95° C. | 30 seconds |
| 56° C. | 30 seconds |
| 72° C. | 10 seconds |
| Goto 2 | 45 times |
| 4° C. | forever |

Figure 11:
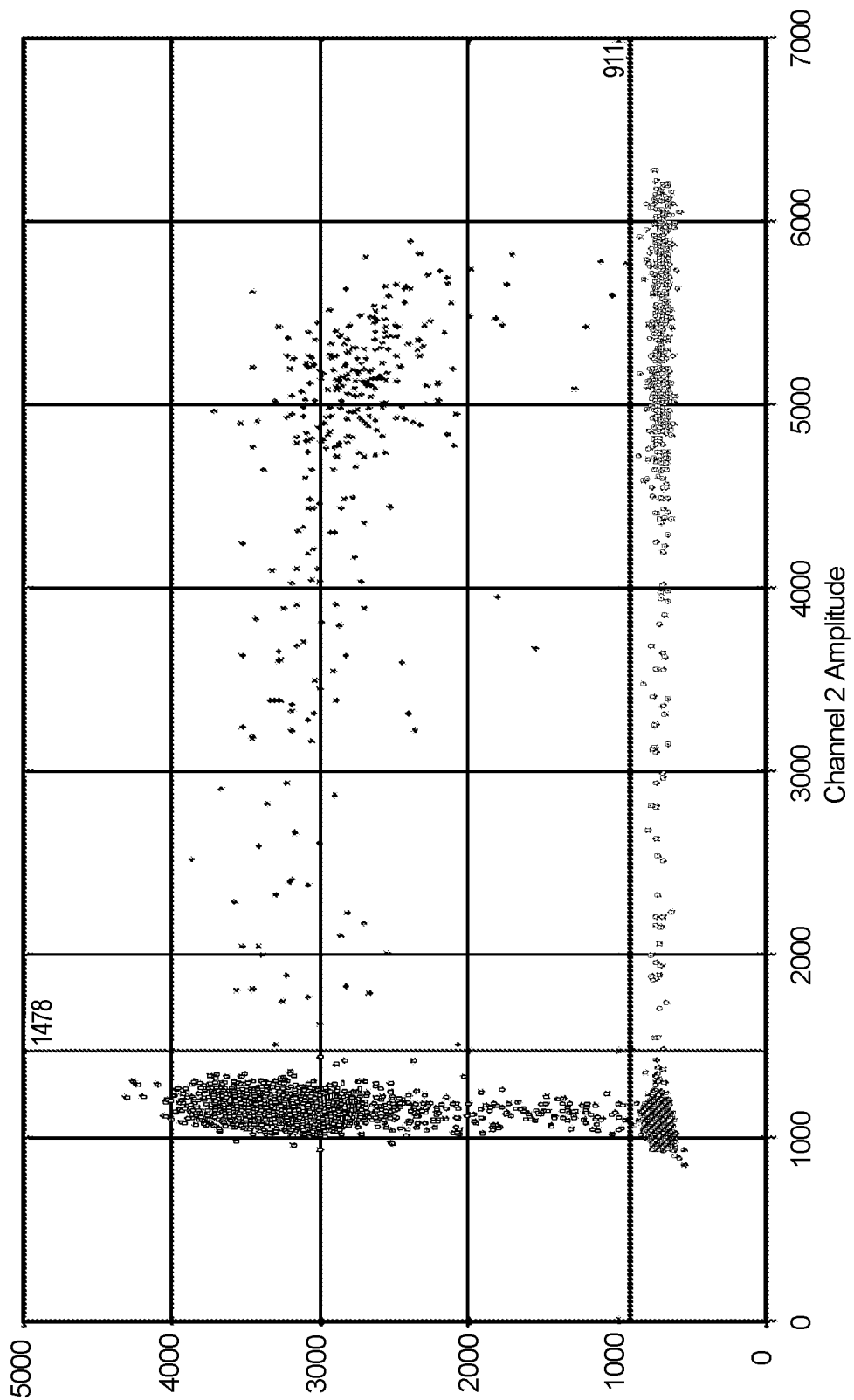
FIG. 11. Two-dimensional cluster plot of ddPCR used to quantify ligation points of 2 MIPs, in which Channel 1 fluorescence (FAM, Telomere ligation points) is plotted vs Channel 2 (HEX, alpha satellite ligation points).

The digital count (FIG. 11) of telomere ligation points formed by MIP-TelF was 551 and 567 copies per µl (duplicate reaction of one sample), and that of centromere alpha satellite ligation points formed by MIP-Centv2 was 95 and 97 copies per μl (duplicate reaction of one sample). Therefore, the indicator values of these duplicates were 5.8 and 5.85, respectively.

REFERENCES CITED

Absalan, Farnaz, and Mostafa Ronaghi. 2007. "Molecular Inversion Probe Assay." Methods in Molecular Biology. doi.org/10.1385/1-59745-515-6:315.
Cawthon, Richard. 2012. Methods of predicting mortality risk by determining telomere length. EP2474822A1.
Cawthon, Richard M. 2009. "Telomere Length Measurement by a Novel Monochrome Multiplex Quantitative PCR Method." Nucleic Acids Research. doi.org/10.1093/nar/gkn1027.
Cawthon, Richard M. 2010. Monochrome multiplex quantitative per. WO2010075413A1.
Cawthon, Richard M. 2010. Reducing non-target nucleic acid dependent amplifications: amplifying repetitive nucleic acid sequences. US7695904.
Cawthon, Richard M., Richard A. Kerber, Sandra J. Hasstedt, and Elizabeth O'Brien. 2011. Methods and kits for determining biological age and longevity based on gene expression profiles. US20110207128A1.
Cawthon, R. M. 2002. "Telomere Measurement by Quantitative PCR." Nucleic Acids Research. doi.org/10.1093/nar/30.10.e47.
Hardenbol, Paul, Johan Bailer, Maneesh Jain, Mats Nilsson, Eugeni A. Namsaraev, George A. Karlin-Neumann, Hossein Fakhrai-Rad, et al. 2003. "Multiplexed Genotyping with Sequence-Tagged Molecular Inversion Probes." Nature Biotechnology. doi.org/10.1038/nbt821.
Harley, Calvin. 2014. Saliva-derived measures of telomere abundance and sample collection device. US20140370505A1.
Harley, Calvin, Jue Lin, and Karl Guegler. 2018. Multiplex quantitative PCR. US9944978.
Keefe, David, Sherman Weissman, Lin Liu, Fang Wang, and Xinghua Pan. 2016. A method for a single cell analysis of telomere length. US20160032360A1.
Litterst, Claudia, Austin P. SO, and Duc Do. 2014. Digital assays with a reporter for amplicon length. WO2014031908A1.
Litterst, Claudia, and Luis A. Ugozzoli. 2016. Digital assay for telomere length. US9347094B2.
Martin-Ruiz, Carmen M., Duncan Baird, Laureline Roger, Petra Boukamp, Damir Krunic, Richard Cawthon, Martin M. Dokter, et al. 2015. "Reproducibility of Telomere Length Assessment: An International Collaborative Study." International Journal of Epidemiology. doi.org/10.1093/ije/dyu191.
Nilsson, Mats, Helena Malmgren, Martina Samiotaki, Marek Kwiatkowski, Bhanu P. Chowdhary, and Ulf Landegren. 1994. "Padlock Probes: Circularizing Oligonucleotides for Localized DNA Detection." Science. doi.org/10.1126/science.7522346.
Syvanen, Ann Christine. 2005. "Toward Genome-Wide Snp Genotyping." Nature Genetics. doi.org/10.1038/ng1558.

```
INFORMAL SEQUENCE LISTING
(MIP-TelF)
                                    SEQ ID NO: 1
5'/Phos/GT TAG GGT TAG GGT TAG GGT TAC TTC AGC TTC

CCG ATC CGA CGG TAG TGT TCA CAC AGG AAA CAG CTA TGA

CTA GGG TTA GGG TTA GGG TT (MIP-TelF+A)
                                    SEQ ID NO: 2
5'Phos/GT TAG GGT TAG GGT TAG GGT TAC TTC AGC TTC

CCG ATC CGA CGG TAG TGT TCA CAC AGG AAA CAG CTA TGA

CTA GGG TTA GGG TTA GGG TTA (ShortMIPtelo)
                                    SEQ ID NO: 3
5'Phos/G GT TAG GGT TAG GGT TAC TTC AGC TTC CCG ATC

CGA CGG TAG TGT TCA CAC AGG AAA CAG CTA TGA C GG

TTA GGG TTA GGG TTA (5' homology region of MIP-TelF, MIP-TelF+A)
                                    SEQ ID NO: 4
GT TAG GGT TAG GGT TAG GGT TA (5' homology region of ShortMIPtelo)
                                    SEQ ID NO: 5
G GT TAG GGT TAG GGT TA (3' homology region of MIP-TelF)
                                    SEQ ID NO: 6
TA GGG TTA GGG TTA GGG TT (3' homology region of MIP-TelF+A)
                                    SEQ ID NO: 7
TA GGG TTA GGG TTA GGG TTA (3' homology region of ShortMIPtelo)
                                    SEQ ID NO: 8
GG TTA GGG TTA GGG TTA (AAGG: MIP-2019AAGG pure)
                                    SEQ ID NO: 9
/5Phos/ggaaggaaggaaggaaggaaggTCGATCCGACAGCTTCCGTagC GgttTCACACAGGAAACAGCTATGACtcacagaaggaaggaaggaaggaag gaag (Long GC_Telo_F)
                                    SEQ ID NO: 10
GGTCCGAGCCAGC TAT GAC TAG GGT TAG GG (longGC_Link_R_tel tail)
                                    SEQ ID NO: 11
gcgcatgtgaATC GGG AAG CTG AAG TAA CC (longGC_M13F+6)
                                    SEQ ID NO: 12
GCTGCCTCGC AGG AAA CAG CTA TGA CTC ACA G (longGC AAGG R)
                                    SEQ ID NO: 13
GGTGCGTCGC GCT GTC GGA TCG ACC TTC CTT (Taqman_long_Telo (FAM))
                                    SEQ ID NO: 14
5'FAM-TA GGG TTA GGG TTA GGG TTA GGGT (Taqman AAGG (HEX))
                                    SEQ ID NO: 15
5'HEX-AAG GAA GGA AGG AAG GAA GG (longGC_M13_F)
                                    SEQ ID NO: 16
ggcgcatggcTCA CAC AGG AAA CAG CTA TGA C (longGC_Link_R_ATGG)
                                    SEQ ID NO: 17
gcatggcgacaATC GGG AAG CTG AAG CCA tccat (Taq-3-Telo--for telomere MIPs)
                                    SEQ ID NO: 18
/56-FAM/TA GGG TTA G/ZEN/G GTT AGG GTT /3IABkFQ
```

(Taq-3-ATGG--for ATGG MIPs)
SEQ ID NO: 19
/5HEX/GG ATG GAT G/ZEN/G ATG GAT GGA T/3IABkFQ (MIP-ATGG)
SEQ ID NO: 20
/5Phos/AT GGA TGG ATG GAT GGA TGG ATG GCT TCA GCT TCC CGA TCC GAC GGT TAG GTT CAC ACA GGA AAC AGC TAT GAC GGA TGG ATG GAT GGA TGG AT (ShortMIP4bp)
SEQ ID NO: 21
/5Phos/G ATG GAT GGA TGG ATG GCT TCA GCT TCC CGA TCC GAC GGT TAG GTT CAC ACA GGA AAC AGC TAT GAC TGG ATG GAT GGA TGG AT (MIP to interrogate [AAGG]n)
SEQ ID NO: 22
5'-GAA GGAA GGAA GGAA GGAA GGGGCGCTTCAGCTTCCCGATCCG ACGGTAGTGTTCA CAC AGG AAA CAG CTA TGA CAA GGAA GGAA GGAA GGAA GG-3'

(MIP-AAGGpure)
SEQ ID NO: 23
/5Phos/GG AAGG AAGG AAGG AAGG AAGG TCG ATC CGA CAG CTT CCG TAG CGG TTT CAC ACA GGA AAC AGC TAT GAC TCA CAG AAGG AAGG AAGG AAGG AAGG AAG (MIP-Centv2)
SEQ ID NO: 24
5'/Phos/gtc TAG GTT TGA TGT GAA GAT Ata ccc gCT TCA GCT TCC CGA TCC GAC GGT agg ttT CAC ACA GGA AAC AGC TAT GAC tCa cag aaA ACG TTC TGA GAA TGC (M13_MIP_L2)
SEQ ID NO: 25
GCGGGCAGGGCGGCtctagaTCACACAGGAAACAGCTATGAC (MIP_LinkC-2Ls)
SEQ ID NO: 26
GGCCCTACCGTCGGATCGGGAAGC (M13_Cent_v2-s)
SEQ ID NO: 27
GGCCTATGACTCACAGAAAACGTTCTGAG (Linker_v2-s)
SEQ ID NO: 28
CTACCGTCGGATCGGGAAG (Taq-cent)
SEQ ID NO: 29
/5HEX/GTC TAG GTT TGA TGT GAA GAT ATA CCC G CTT/3IABkFQ/

(Example LL-MIP product after cloning of a PCR product, which shows 6 MIP probes were ligated together in this LL-MIP)
SEQ ID NO: 30
GCGCATGTGAATCGGGAAGCTGAAGTAACCCTAACCCTAACCCTAACCCTA
ACCCTAACCCTAACCCTAGTCATAGCTGTTTCCTGTGTGAACACTACCGTC
GGATCGGGAAGCTGAAGTAACCCTAACCCTAACCCTAACCCTAACCCTAAC
CCTAGTCATAGCTGTTTCCTGTGTGAACACTACCGTCGGATCGGGAAGCTG
AAGTAACCCTAACCCTAACCCTAACCCTAACCCTAACCCTAACCCTAGTCA
TAGCTGTTTCCCGTGTGAACACTACCGTCGGATCGGGAAGCGAAGTAACCC
TAACCCTAACCCTAACCCTAACCCTAACCCTAGTCATAGCTGTTTCCTGTG
TGAACACTACCGTCGGATCGGAAGCTGAATAACCCTAACCCTAACCCTAAC
CCTAACCCTAACCCTAACCCTAGTCATAGCTGTTTCCTGTGTGAACACTAC
CGTCGGATCGGGAAGCTGAAGTAACCCTAACCCTAACCCTAACCCTAACCC
TAACCCTAACCCTAGTCATAGCTGTTTCCTGTGTGAGCCATGCGCC Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of determining the copy number of a tandem repeat sequence in an individual's genome, the method comprising:
   i) providing a first single-stranded DNA probe and a second single-stranded DNA probe, each comprising:
   (1) a 5' homology region that extends to the 5' end of the DNA probe and comprises a nucleotide sequence complementary to a tandem repeat sequence;
   (2) a linker region; and
   (3) a 3' homology region that extends to the 3' end of the DNA probe and comprises a nucleotide sequence complementary to the tandem repeat sequence, such that the 5' homology region and 3' homology region can bind to the same strand of a template DNA comprising the tandem repeat sequence,
   wherein upon binding of the 5' homology region and the 3' homology region to the same strand of a template DNA such that the 3' homology region is immediately 3' of the 5' homology region within a single repeat unit on the template DNA, the 3' end of the 3' homology region and the 5' end of the 5' homology region are thus separated by a nucleotide gap of less than one complete repeat unit on the template DNA, the nucleotide gap of less than one complete repeat unit comprises at most two different bases,
   wherein the 5' and 3' homology regions of the first DNA probe are complementary to a first tandem repeat sequence with a copy number that varies in an individual's genome,
   wherein the 5' and 3' homology regions of the second DNA probe are complementary to a second tandem repeat sequence with a copy number that does not vary in an individual's genome, and
   wherein the at most two bases comprised by the nucleotide gap of the first DNA probe are also comprised by the nucleotide gap of the second DNA probe;
   ii) contacting a biological sample from the individual with a plurality of the first DNA probes and a plurality of the second DNA probes in the presence of a DNA polymerase, ligase activity, and at most two deoxyribonucleoside triphosphates corresponding to the bases comprised in the nucleotide gaps of the first and second DNA probes under conditions conducive to extension of the 3' end of a DNA probe and ligation to the 5' end of the DNA probe bound to the same template, to extend the 3' end of the first and second DNA probes and ligate to the 5' end of the first and second DNA probes, respectively, and generate a first and second circularized and ligated linear probe products;

iii) quantifying the first and second circularized and ligated linear probe products generated in step ii); and iv) normalizing the quantity of the first circularized and ligated linear probe products over the quantity of the second circularized and ligated linear probe products to determine the copy number of the first tandem repeat sequence in the individual's genome.

2. The method of claim 1, wherein the nucleotide sequences of the 5' and 3' homology regions of the first and second probes are 100% complementary to the first and second tandem repeat sequences, respectively.

3. The method of claim 1, wherein the 5' and 3' homology regions of the probes are 15-25 nucleotides long.

4. The method of claim 1, wherein the first tandem repeat sequence is a telomere sequence.

5. The method of claim 4, wherein the telomere sequence is a human telomere sequence.

6. The method of claim 1, wherein the linker region of each the probes comprises one or more sequence elements selected from the group consisting of a common primer sequence, a probe-specific primer sequence, a TaqMan probe sequence, and a tag sequence.

7. The method of claim 1, wherein the 3' end of the 3' homology region and the 5' end of the 5' homology region of the first DNA probe are separated by a gap of 1 or 2 nucleotides when bound within a single repeat unit on the tandem repeat sequence, wherein the 1 or 2 nucleotides comprise a single base, and wherein only one deoxyribonucleoside triphosphate corresponding to the single base is provided in step ii).

8. The method of claim 7, wherein the single base is G.

9. The method of claim 1, wherein the 3' end of the 3' homology region of the second DNA probe and the 5' end of the 5' homology region of the first DNA probe or the 3' end of the 3' homology region of the first DNA probe and the 5' end of the 5' homology of the second DNA probe are separated by a gap of 3 nucleotides when bound within a single repeat unit on the tandem repeat sequence, wherein the 3 nucleotides comprise 2 bases, and wherein two deoxyribonucleoside triphosphates corresponding to the two bases are provided in step (ii).

10. The method of claim 9, wherein the 2 bases are A and G.

11. The method of claim 1, wherein the 5' homology region of the first DNA probe of step i) comprises the nucleotide sequence of SEQ ID NO:4 or SEQ ID NO:5.

12. The method of claim 1, wherein the 3' homology region of the first DNA probe of step i) comprises the nucleotide sequence of any one of SEQ ID NOs:6-8.

13. The method of claim 1, wherein the first DNA probe comprises the nucleotide sequence of any one of SEQ ID NOs:1-3.

14. The method of claim 1, wherein a large excess of the first and second DNA probes are provided relative to the quantity of genomic DNA in the biological sample.

15. The method of claim 1, wherein no exonuclease is added during steps i) to iv).

16. The method of claim 1, wherein the only exonuclease added during steps i) to iv) is exonuclease I, and wherein the level of exonuclease I does not exceed 20 units per 50 ng of genomic DNA and is present for a maximum of one hour.

17. The method of claim 1, wherein the quantities of the circularized and ligated linear probe products are determined using a method selected from the group consisting of quantitative PCR, digital PCR, and sequencing.

* * * * *